US007736640B2

(12) United States Patent
Lorence et al.

(10) Patent No.: US 7,736,640 B2
(45) Date of Patent: *Jun. 15, 2010

(54) METHODS OF TREATING AND DETECTING CANCER USING VIRUSES

(75) Inventors: Robert M. Lorence, Chicago, IL (US); Kirk W. Reichard, Chicago, IL (US)

(73) Assignee: Wellstat Biologics Corporation, Gaithersburg, MD (US)

( * ) Notice: Subject to any disclaimer, the term of this patent is extended or adjusted under 35 U.S.C. 154(b) by 595 days.

This patent is subject to a terminal disclaimer.

(21) Appl. No.: 11/441,201

(22) Filed: May 26, 2006

(65) Prior Publication Data

US 2006/0216310 A1 Sep. 28, 2006

Related U.S. Application Data

(63) Continuation of application No. 08/260,536, filed on Jun. 16, 1994, now Pat. No. 7,056,689, which is a continuation-in-part of application No. 08/055,519, filed on Apr. 30, 1993, now abandoned.

(51) Int. Cl.
A61K 48/00 (2006.01)
(52) U.S. Cl. .................................................. 424/93.2
(58) Field of Classification Search ........................ None
See application file for complete search history.

(56) References Cited

U.S. PATENT DOCUMENTS

| 3,577,525 | A | 5/1971 | Baker |
| 4,053,582 | A | 10/1977 | Stickl |
| 4,108,983 | A | 8/1978 | Wallack |
| 4,126,671 | A | 11/1978 | House et al. |
| 4,282,315 | A | 8/1981 | Luderer et al. |
| 4,334,016 | A | 6/1982 | Furukawa |
| 4,379,839 | A | 4/1983 | Spiegelman |
| 4,391,911 | A | 7/1983 | Tarro |
| 4,405,712 | A | 9/1983 | Vande Woude et al. |
| 4,465,769 | A | 8/1984 | Hampar et al. |
| 4,571,385 | A | 2/1986 | Greenberg et al. |
| 4,582,787 | A | 4/1986 | 'Frankel |
| 4,647,773 | A | 3/1987 | Gallo et al. |
| 4,735,895 | A | 4/1988 | Kopeiovich |
| 4,748,109 | A | 5/1988 | Baird |
| 4,757,000 | A | 7/1988 | Tohmatsu et al. |
| 4,777,127 | A | 10/1988 | Suni et al. |
| 4,786,590 | A | 11/1988 | McGrath et al. |
| 4,839,288 | A | 6/1989 | Montagnier et al. |
| 4,849,334 | A | 7/1989 | Lorincz |
| 4,861,719 | A | 8/1989 | Miller |
| 4,861,720 | A | 8/1989 | Pedersen et al. |
| 4,908,306 | A | 3/1990 | Lorincz |
| 4,912,030 | A | 3/1990 | Weiss et al. |
| 4,970,071 | A | 11/1990 | McMichael |
| 5,037,753 | A | 8/1991 | Pedersen et al. |
| 5,045,447 | A | 9/1991 | Minson |
| 5,057,314 | A | 10/1991 | Whitfill et al. |
| 5,075,213 | A | 12/1991 | Pande et al. |
| 5,077,198 | A | 12/1991 | Shih et al. |
| 5,124,148 | A | 6/1992 | Csatary et al. |
| 5,142,032 | A | 8/1992 | Grimmel et al. |
| 5,169,753 | A | 12/1992 | Ng et al. |
| 5,192,539 | A | 3/1993 | Van der Marel et al. |
| 5,215,745 | A | 6/1993 | Csatary et al. |
| 5,252,479 | A | 10/1993 | Srivastava |
| 5,273,745 | A | 12/1993 | Schirrmacher |
| 5,310,678 | A | 5/1994 | Bingham et al. |
| 5,739,107 | A | 4/1998 | Cohen et al. .................. 514/12 |
| 7,056,689 | B1 * | 6/2006 | Lorence et al. ............ 435/7.23 |
| 2003/0044384 | A1 | 3/2003 | Roberts et al. ............. 424/93.2 |
| 2003/0165465 | A1 | 9/2003 | Roberts et al. ............. 424/93.2 |
| 2004/0131595 | A1 * | 7/2004 | Lorence et al. ............ 424/93.2 |

FOREIGN PATENT DOCUMENTS

| DE | 2154202 | 10/1971 |
| EP | 235004 | 9/1987 |
| EP | 0 292 293 | 11/1988 |
| EP | 0 292 293 A2 | 11/1988 |
| EP | 0 292 293 A3 | 11/1988 |
| EP | 331939 | 9/1989 |
| EP | 342128 | 11/1989 |
| EP | 396734 | 9/1990 |
| JP | 58-116422 | 7/1958 |
| JP | 58116422 | 7/1983 |
| WO | WO 86/00529 | 1/1986 |
| WO | WO 86/00811 | 2/1986 |
| WO | WO 87/03451 | 6/1987 |
| WO | WO 91/09866 | 7/1991 |
| WO | WO 93/18790 | 9/1993 |
| WO | WO 94/18992 | 9/1994 |
| WO | WO 94/21798 | 9/1994 |
| WO | WO 9421798 | 9/1994 |

OTHER PUBLICATIONS

08/260536 file history.*
Schloer, et al., "Relationship of Plaque Size and Virulence for Chickens of 14 Representative Newcastle Disease Virus Strains", Journal of Virology, 2(1): 40-47, 1968.*
Hanson, et al., "Identification of vaccine strains of Newcastle disease virus", Science, 122(3160): 156-157, 1955.*
Reichard, et al., "Newcastle Disease Virus Selectively Kills Human Tumor Cells", Journal of Surgical Research, 52: 448-453, May 1992.*

(Continued)

Primary Examiner—Emily M. Le
(74) Attorney, Agent, or Firm—Douglas A. Golightly

(57) ABSTRACT

The invention provides a method of treating cancer in a mammal comprising administering to the mammal an effective amount of virus, particularly Newcastle Disease Virus or other Paramyxovirus. The invention also provides a method of treating cancer in a mammal comprising administering such viruses to the mammal in combination with another agent such as a chemotherapeutic compound, immunoadjuvant, cytokine, or immunosuppressive agent. The invention further provides a method of detecting cancer cells in a mammal using Paramyxovirus as an imaging agent and as an indicator of cancer cell growth in the mammal. The invention further provides genetically engineered Paramyxoviruses, and kits containing the viral compositions disclosed by the invention.

25 Claims, 14 Drawing Sheets

OTHER PUBLICATIONS

Reichard, et al., "N-myc Oncogene Enhances the Sensitivity of Neuroblastoma to Killing by Newcastle Disease Virus", Surg Forum Pediatric Surgery, 43: 603-606, 1992.*

Berkner, et al., "Development of Adenovirus Vectors for the Expression of Heterologous Genes," Bio Techniques, 6:616-629, 1988.*

Berns, "Parvoviridae and Their Replication", Fundamental Virology 2nd edition, Chapter 32: 817-837, 1991.*

Bett, et al., "Packaging capacity and stability of human adenovirus type 5 vectors", J Virol. 67(10): 5911-5921, Oct. 1993.*

Chengalvala, et al., "Evaluation of adenovirus type 4 and type 7 recombinant hepatitis B vaccines in dogs", Vaccine, 9(7): 485-490, 1991.*

Di Luca, et al., "Simultaneous presence of herpes simplex and human papilloma virus sequences in human genital tumors", Int J Cancer, 40:763-768, 1987.*

Holzaepfel, et al., "The use of APC3 virus as a cancericidal agent; preliminary report", Cancer. 10(3): 577-80, 1957.*

Kaufman, et al., "Herpesvirus-induced antigens in squamous-cell carcinoma in situ of the vulva", N Engl J Med., 305(9):483-488, 1981.*

Li, et al., "Priming with recombinant influenza virus followed by administration of recombinant vaccinia virus induces CD8+ T-cell-mediated protective immunity against malaria", Pro Natl Acad Sci, 90(11): 5214-8, Jun. 1993.*

Lyerly, et al., "Gene delivery systems in surgery", Arch Surg., 128(11): 1197-1206, Nov. 1993.*

McDougall, et al., "Herpesvirus-specific RNA and protein in carcinoma of the uterine cervix", Proc. Natl. Acad. Sci., 79(12): 3853-3857, 1982.*

Millar, et al., "Molecular Cloning and Nucleotide Sequencing of Newcastle Disease Virus", Newcastle Disease, Kluwer Academic Publishers, Chapter 5: 79-97, 1988.*

Miller, "Human gene therapy comes of age", Nature, 357(6378): 455-460, Jun. 1992.*

Natuk, et al., "Adenovirus-human immunodeficiency virus (HIV) envelope recombinant vaccines elicit high-titered HIV-neutralizing antibodies in the dog model", Proc Natl Acad Sci, 89(16): 7777-7781, Aug. 1992.*

Park, et al., "Rescue of a foreign gene by Sendai virus", Proc Natl Acad Sci, 88(13): 5537-5541, 1991.*

Pattnaik, et al., "Infectious defective interfering particles of VSV from transcripts of a cDNA clone", Cell, 69(6): 1011-20, Jun. 1992.*

Ramshaw, et al., "Expression of cytokines by recombinant vaccinia viruses: a model for studying cytokines in virus infections in vivo", Immunol Rev., 127: 157-182; Jun. 1992.*

Shingu, et al., "Therapeutic effects of bovine enterovirus infection on rabbits with experimentally induced adult T cell leukaemia", J Gen Virol., 72( Pt 8): 2031-2034, 1991.*

Taniguchi, et al., "Structure and expression of a cloned cDNA for human interleukin-2", Nature, 302(5906): 305-310, 1983.*

Tratschin, et al., "A human parvovirus, adeno-associated virus, as a eucaryotic vector: transient expression and encapsidation of the procaryotic gene for chloramphenicol acetyltransferase", Mol Cell Biol., 4(10): 2072-2081, 1984.*

Xiong, et al., "Sindbis virus: an efficient, broad host range vector for gene expression in animal cells", Science, 243(4895):1188-1191, 1989.*

Asada, "Treatment of human cancer with mumps virus", Cancer, 34: 1907-1928, 1974.*

Bluming, et al., "Regression of Burkitt's lymphoma in association with measles infection", Lancet, 2(7715): 105-106, 1971.*

Bohle, et al., "Postoperative active specific immunization in colorectal cancer patients with virus-modified autologous tumor-cell vaccine. First clinical results with tumor-cell vaccines modified with live but avirulent Newcastle disease virus", Cancer. 66(7): 1517-1523, 1990.*

Cascino, et al., University Research Week: Apr. 14-16, Poster No. P54 1992.*

Cassel, et al., "Newcastle Disease Virus as an Antineoplastic Agent", Cancer, 18: 863-868, 1965.*

Cassel, et al., "A phase II study on the postsurgical management of Stage II malignant melanoma with a Newcastle disease virus oncolysate", Cancer, 52(5): 856-860; 1983.*

Csatary, "Viruses in the treatment of cancer", Lancet, 2(7728): 825, 1971.*

De Pace, "Sulla sacomparsa di un enorme cancro vegetante del callo dell'utero senza cura chirurgica", Ginecologia, 9: 82-88, 1912.*

Gross, "Measles and leukaemia" Lancet, 1(7695): 397-398, 1971.*

Lorence, et al., University Research Week: Apr. 16-18, Poster No. 93, 1991.*

Lorence, et al., "Ras-Transformation of Human Fibroblasts enhances Cytotoxicity and Replication by Newcastle disease Virus (NDV)", Proc. Am. Assoc. Cancer Res. 33: 398, Mar. 1992.*

Murray, et al., "Viral oncolysate in the management of malignant melanoma. II. Clinical studies", Cancer, 40(2):680-686, 1977.*

Pasquinucci, "Possible effect of measles on leukaemia", Lancet, 1(7690): 136, 1971.*

Paulson, et al., "Restoration of Specific Myxovirus Receptors to Asialoerythrocytes by Incorporation of Sialic Acid with Pure Sialyltransferases", J Biol. Chem., 254(6): 2120-2124, 1979.*

Reichard, et al., "Retinoic acid enhances killing of neuroblastoma cells by Newcastle disease virus", J Pediatr Surg, 28(10): 1221-1225, Oct. 1993.*

Reichard, et al., "Newcastle Disease Virus Selectively Kills Human Tumor Cells", The Association for Academic Surgery, Twenty-Fifth Annual Meeting, Colorado Springs, Colorado, p. 152, 1991.*

Reichard, et al., University Research Week: Apr. 13-15; Poster No. 100, 1993.*

Reichard, et al., "Selective replication of Newcastle disease virus in cancer cells is associated with virus-induced cell fusion," Proc Am Assoc Cancer Res., 33: 521, 1992.*

Salmon, et al., Compt. Rend. Soc. Biol., 86, pp. 819-820, 1922 (no translation).*

Weiss, et al., "Polyadenylate sequences on Newcastle disease virus mRNA synthesized in vivo and in vitro", J. Virol, 13(6): 1220-1230, 1974.*

Austin, et al., "Virus augmentation of the antigenicity of tumor cell extracts", Adv Cancer Res, 30: 301-305, 1979.*

Cassel, et al., "Viral oncolysate in the management of malignant melanoma. I. Preparation of the oncolysate and measurement of immunologic responses", Cancer, 40(2): 672-679, 1977.*

Cukor, et al., "Effect of adeno-associated virus on cancer expression by herpesvirus-transformed hamster cells", J Natl Cancer Inst, 55(4): 957-959, 1975.*

Culver, et al., "In vivo gene transfer with retroviral vector-producer cells for treatment of experimental brain tumors", Science, 256(5063): 1550-1552, Jun. 1992.*

Dupressoir, et al., "Inhibition by parvovirus H-1 of the formation of tumors in nude mice and colonies in vitro by transformed human mammary epithelial cells", Cancer Res, 15;49(12): 3203-3208, 1989.*

Heicappell, et al., "Prevention of metastatic spread by postoperative immunotherapy with virally modified autologous tumor cells. I. Parameters for optimal therapeutic effects", Int J Cancer, 37(4): 569-577, 1986.*

Kenney, et al., "Viruses as oncolytic agents: a new age for "therapeutic" viruses?", J Natl Cancer Inst., 86(16):1185-1186, 1994.*

Kobayashi, et al., "Viral xenogenization of intact tumor cells", Adv Cancer Res., 30:279-299, 1979.*

Lorence, et al., "Newcastle disease virus as an antineoplastic agent: induction of tumor necrosis factor-alpha and augmentation of its cytotoxicity", J Natl Cancer Inst., 80(16):1305-1312, 1988.*

Lorence, et al., "Complete regression of human neuroblastoma xenografts in athymic mice after local Newcastle disease virus therapy", J Natl Cancer Inst., 86(16): 1228-1233, 1994.*

Moore, "Effects of Viruses on Tumors" Annual Review of Microbiology, 8(1): 393-410, 1954.*

Ram, et al., "In Situ Retroviral-mediated Gene Transfer for the Treatment of Brain Tumors in Rats", Cancer Research, 53: 83-88, Jan. 1993.*

Rommelaere, et al., "Antineoplastic activity of parvoviruses", J Virol Methods, 33(3):233-251, 1991.*

Rukavishnikova, et al., "Some immunological mechanisms of the influenza virus antitumour effect", Acta Virol., 20(5): 387-394, 1976.*

Shingu, et al., "Therapeutic effects of bovine enterovirus infection on rabbits with experimentally induced adult T cell leukaemia", J Gen Virol., 72(Pt 8): 2031-4, 1991.*

Sinkovics, J. G, et al., "Superinfection of tumors with viruses", Experientia 25, 733-734, 1969.*

Huebner, et al., "Studies on the use of viruses in the treatment of carcinoma of the cervix", Cancer, 9(6): 1211-1218, 1956.*

Suskind, et al., "Viral agents oncolytic for human tumors in heterologous host; oncolytic effect of Coxsackie B viruses", Proc Soc Exp Biol Med., 94(2):309-318, 1957.*

Taylor, et al., "Virus-induced regression of tumor growth", J Natl Cancer Inst.; 44(3): 515-519, 1970.*

Telerman, et al., "A model for tumor suppression using H-1 parvovirus", Proc Natl Acad Sci, 90(18): 8702-6, Sep. 1993.* von Hoegen, et al., "Modification of tumor cells by a low dose of Newcastle disease virus. Augmentation of the tumor-specific T cell response in the absence of an anti-viral response", Eur J Immunol. 18(8): 1159-1166, 1988.*

Walz, et al., "Adeno-associated virus sensitizes HeLa cell tumors to gamma rays", J Virol. 66(9): 5651-7, Sep. 1992.*

Wheelock, et al., "Observations on the Repeated Administration of Viruses to a Patient with Acute Leukemia: A Preliminary Report", N Engl J Med., 271: 645-651, 1964.*

Cassel, "Immunodiagnosis and Immunotherapy: Carcinoma of the Kidney", Urologic Oncology, pp. 236-242, 1988.*

Cassel, et al., "Letter to the Editor", Nat. Immun. Cell Growth Regul; 7: 351-352, 1988.*

Csatary, et al., "Attenuated veterinary virus vaccine for the treatment of cancer", Cancer Detect Prev., 17(6):619-627, 1993.*

Jai, et al., "Selective Destruction of Gliomas in Immunocompetent Rats by Thymidine Kinase-Defective Herpes Simplex Virus Type 1", Journal of the National Cancer Institute, 86(16): 1209-1215, 1994.*

Mineta, et al., "Treatment of malignant gliomas using ganciclovir-hypersensitive, ribonucleotide reductase-deficient herpes simplex viral mutant", Cancer Res, 54(15): 3963-3966, 1994.*

Okuna, et al., "Studies on the use of mumps virus for treatment of human cancer", Biken Journal, 21(2): 37-49, 1978.*

Lorence, et al., "Newcastle disease virus selectively binds to and kills cervical carcinoma cells in cultures mixed with normal fibroblasts", Proc. Am. Assoc. Cancer Res., 34: 377, Mar. 1993.*

Schirrmacher, et al., "Successful application of non-oncogenic viruses for antimetastatic cancer immunotherapy", Cancer Rev 5: 19-49, 1986.s.*

Clercq, E.D., et al; "Current Concepts of Interferon and Interferon Induction"; Division of Infectious Diseases, Dept. of Medicine, Stanford University School of Medicine, Stanford, California; pp. 17-46 (1970).

Hilleman, M.R.; "Interferon Induction and Utilization"; J. Cell Physiol.; vol. 71 pp. 43-60 (1968).

Eaton, M.D., et al; "Contribution of Antiviral Immunity to Oncolysis by Newcastle Disease Virus in a Murine Lymphoma"; Journal of the National Cancer Institute; vol. 39, No. 1-6 pp. 1089-1097 (1967).

Dalgleish, A.G., et al; "The Development of Therapeutic Vaccines for the Management of Malignant Melanoma"; Cancer Surveys, vol. 26; pp. 289-319 (1996).

Japanese Patent Office; Public Patent Disclosure Bulletin No. S51-73117; Bulletin Date Jun. 24, 1976; Patent Application No. S49-147261; Patent Application Date; Dec. 19, 1974, (6 pgs).

Nature New Biology; vol. 245, No. 147, Oct. 24, 1973, Role of Interferon in the Anti-Melanoma Effects of Poly (I), Poly (C) and Newcastle Disease Virus; pp. 229-230.

Baars, A., et al; "Skin tests predict survival after autologous tumor cell vaccination in metastatic melanoma: Experience in 81 patients"; Annals of Oncology; vol. 11, pp. 965-970 (2000).

Schirrmacher, V.; "In situ analysis of tumor-specific CTL effector and memory responses elicited by tumor vaccination"; International Journal of Oncology; vol. 15; pp. 27-227 (1999).

Vile, R.G.; "Vironcology-not yet, but soon?"; Nature Biotechnology, Nature Publishing Group; vol. 19 pp. 1020-1022, (2001).

Yotnda, P., et al; "Targeted delivery of adenoviral vectors by cytotoxic T cells"; Blood; vol. 104, No. 8, pp. 2272-2280 (2004).

Harrington, K., et al; "Cells as Vehicles for Cancer Gene Therapy: The Missing Link Between Targeted Vectors and Systemic Delivery"; Human Gene Therapy; vol. 13; pp. 1263-1280 (2002).

Crystal, R.G., et al; "Analysis of Risk Factors for Local Delivery of Low- and Intermediate-Dose Adenovirus Gene Transfer Vectors to Individuals with a Spectrum of Comorbid Conditions"; Human Gene Therapy; vol. 13; pp. 65-100 (2002).

Chen, Y., et al; "Pre-Existent Adenovirus Antibody Inhibits Systemic Toxicity and Antitumor Activity of CN706 in the Nude Mouse LNCaP Xenograft Model: Implications and Proposals for Human Therapy"; Human Gene Therapy; vol. 11; pp. 1553-1567 (2000).

Jia, W., et al; "Viral Vectors for Cancer Gene Therapy: Viral Dissemination and Tumor Targeting"; Current Gene Therapy; vol. 5, pp. 133-142 (2005).

Morrissey, R.E., et al.; "Rodent Nonclinical Safety Evaluation Studies of SCH 58500, an Adenoviral Vector for the p53 Gene"; Toxicological Sciences; vol. 65, pp. 266-275 (2002).

Plager, C., et al; "Adjuvant Immunotherapy of M.D. Anderson Hospital (MDAH Stage III-B Malignant Melanoma with Newcastle Disease Virus Oncolysate"; Proceedings of American Society of Clinical Oncology; vol. 9 p. 281; #1091 (Mar. 1990)1.

Leibrich, W., et al; "In vitro and Clinical Characterisation of a Newcastle Disease Virus-modified Autologous Tumour Cell Vaccine for Treatment of Colorectal Cancer Patients"; Eur J. Cancer; vol. 27, No. 6, pp. (703-710 (1991).

Mallmann, P.; Autologous Tumor-Cell Vaccination and Lymphokine-Activated Tumor-Infiltrating Lymphocytes (LAK-TIL); Hybridoma; vol. 12, No. 5, pp. 559-566 (1993).

Murray, D.R., et al; "Viral Oncolysate in the Management of Malignant Melanoma II. Clinical Studies"; Cancer; vol. 46, No. 2; pp. 680-686 (1977).

Database WPI; Section Ch. Week 197632; Derwent Publications Ltd., London, GB; AN 1976-60708X; JP 51 073117 A; (Osaka Univ. Microbia); Jun. 24, 1976; XP-002301780 (Abstract).

Database Caplus; Chemical Abstracts Service, Columbus, OH; AN 1992:104333 Caplus; CN 1054 192 A; Sep. 4, 1991; XP-002915850 (Abstract).

Povlsen, C.O.; "Status of Chemotherapy, Radiotherapy, Endocrine Therapy, and Immunotherapy Studies of Human Cancer in the Nude Mouse"; The Nude Mouse in Experimental and Clinical Research; Academic Press, New York, San Francisco, London; pp. 437-457 (1978).

Thorne, S.H., et al; "Future Directions for the Field of Oncolytic Virotherapy: A Perspective on the Use of Vaccinia Virus"; Expert Opin. Biol. Ther.; vol. 4, No. 8; pp. 1307-1321 (2004).

Poster (ASCO Meeting); "Slow Intravenous Infusion of PV701, An Oncolytic Virus: Final Results of a Phase Study"; 2004 Am. Soc. Clin. Oncology (ASCO) Mtg.

Schirrmacher, V., et al; "Virus Potentiation of Tumor Vaccine T-Cell Stimulatory Capacity Requires Cell Surface Binding but not Infection"; Clinical Cancer Research; vol. 3; pp. 1135-1148 (1997).

Zorn, U., et al; "Induction of Cytokines and Cytotoxicity Against Tumor Cells by Newcastle Disease Virus"; Cancer Biotherapy; vol. 9, No. 3; pp. 225-235 (1994).

Zorn, U., et al; "Active Specific Immunotherapy of Renal Cell Carcinoma: Cellular and Humoral Immune Responses"; Cancer Biotherapy & Radiopharmaceuticals; vol. 12, No. 3; pp. 157-165 (1997).

Plager, C., et al; "Adjuvant Immunotherapy with Newcastle Disease Virus Oncolysate of M.D. Anderson (MDAH) Stage III-B Malignant Melanoma"; Head and Neck, Sarcoma, Melanoma, and Other Solid Tumors; Proceedings of ASCO; vol. 4; C-584 p. 150 (1985).

Plager, C., et al; "Adjuvant Immunotherapy with Newcastle Disease Virus Oncolysate of M.D. Anderson (MDAH) Stage III-B Malignant Melanoma"; Head and Neck, Sarcoma, Melanoma, and Other Solid Tumors; Proceedings of ASCO; vol. 5; 534 p. 137 (1986).

Krishnamurthy, S., et al; "Newcastle Disease Virus as an Oncolytic Agent: Mechanism of Viral Infection, Growth and Oncolysis"; American Society for Virology 21$^{st}$ Annual Meeting, University of Kentucky, Lexington, KY, Jul. 20-24, 2002, Scientific Program and Abstracts; p. 90.

Batliwalla, F.M., et al; "A 15-Year Follow-up of AJCC Stage III Malignant Melanoma Patients Treated Postsurgically with Newcastle Disease Virus (NDV) Oncolysate and Determination of Alternations in the CD8 T Cell Repertoire"; *Molecular Medicine*; vol. 4; pp. 783-794 (1998).

Bonaccorsi, P., et al; "Management of High-risk Melanoma"; *Medical Dermtology*; vol. 19, No. 4; pp. 727-735 (2001).

Zhenxiang et al; *Acta Acad. Med. Sinicae*; "I. Results of Treatment on Virus of Ehrlich and S180 Ascitic Tumor Cells"; 6, 1984 (Abstract).

Kirn, D.H. et al; *Molecular Medicine Today*, "Replicating Viruses as Selective Cancer Therapeutics"; Dec. 1996, pp. 519-527.

Zhenxiang et al; *Acta Acad. Med. Sinicae*; "I. Results of Treatment on Virus of Ehrlich and S180 Ascitic Tumor Cells"; 6, 1984 (Abstract).

Sharkey et al; The Nude Mouse in Experimental and Clinical Research, Academic Press, New York, vol. 1, pp. 187-214.

Shirrmacher, *Seminars in Oncology*; "Immunization With Virus-Modified Tumor Cells"; vol. 25, No. 6 (Dec.), 1998; pp. 677-696.

Gesser, I., et al; "Exogenous Interferon and Inducers of Interferon in the Treatment of Balb/c Mice Inoculated with $RC_{19}$ Tumour Cells"; Nature; vol. 223, Aug. 23, 1969; pp. 844-845.

Zhang, Jian-Feng, et al; "Treatment of a human breast cancer xenograft with an adenovirus vector containing an interferon gene results in rapid regression due to viral oncolysis and gene therapy"; Proc. Natl. Acad. Sci. USA, Apr. 1996, vol. 93, pp. 4513-4518.

Kirn, D.H., et al; "Replicating viruses as selective cancer therapeutics"; Molecular Medicine Today, Dec. 1996, pp. 519-527.

Zhang, B.; "Attenuated newcastle disease virus for induction of interferons to combat neoplasm or viral diseases"; (1992); Chemical Abstracts 116:104333.

Pecora, et al, J. Clin. Oncol. (2002) 20(9): 2251-2266.

G.S. Reddy et al; "Use of BHK Cell Culture-Adapted Newcastle Disease Virus for Immunization of Chicks"; 1992; XP-002237247 (Abstract).

G.S. Reddy et al; "Comparison of Two Experimental Binary Ethylenimine Bei Inactivated Newcastle Disease Oil-Emulsion Vaccines"; 1991; XP-002237248 (Abstract).

J. Gelg Jr. et al; "Pathogenicity and Cross-Protection of Pigeon Paramyxovirus 1 and Newcastle Disease Virus in Young Chickens"; (1987); XP-002237249 (Abstract).

M.A. Shuaib et al; "Studies on the Development of Pelleted Newcastle Disease Virus Vaccine"; (1985); XP-002237250 (Abstract).

M.A. Al Imadi et al; "The Susceptibility of Domestic Waterfowl to Newcastle Disease Virus and Their Role in its Spread"; (1982) (Rec'd 1983); XP-002237251 (Abstract).

B. Rivetz et al; "Enzymatic Changes in Serum and Tissues in Fowl Infected with a Neurotropic Mesogenic Strain of Newcastle Disease Virus"; (1982); XP-002237252 (Abstract).

B. Lomniczi; "Properties of Nonneurovirulent Plaque Forming Mutants of Newcastle Disease Virus"; (1976); XP-002237253 (Abstract).

D.Y. Perey et al; "Host Resistance Mechanisms to Newcastle Disease Virus in Immunodeficient Chickens" (38540); (1975); XP-002237254 (Abstract).

I. Szeri, et al; "Effect of Microbial Immunomodulants on the Course of LCMV Infection in Old Mice with Thymus Involutin"; (1992); XP-002237255 (Abstract).

P.B. Spradbrow et al; "Oral Newcastle Disease Vaccination with V4 Virus in Chickens"; Aust. Vet. J., (1991) vol. 68, No. 3, pp. 114-115; XP-002237256; (Abstract).

E.I. Ugochukwu; "Caecal Coccidiosis in Chicks Following Intramuscular Vaccination Against Newcastle Disease"; Bull. Anim. Health Prod. Afr., (1982) vol. 30, No. 4, pp. 353-357; XP-002237257; (Abstract).

W. Leuthgen; "Detection of Antibodies in the Tracheal Exudate of Chicken After Infection with Newcastle Virus"; Immunologie (1972), 144(3), 273-80; XP-002237258 (Abstract).

Hanson et al; "Identification of Vaccine Strains of Newcastle Disease Virus"; Science, vol. 156, 1955, pp. 156-157; XP002237246.

Ahlert et al; "Isolation of a Human Melanoma Adapted Newcastle . . . ,"; *Cancer Research*; 50:5962-5968, 1990.

Eaton et al; "Contribution of Antiviral Immunity to Oncolysis by Newcastle Disease Virus in a Murine Lymphoma"; *Journal of the National Cancer Institute*; 39(6):1089-1097 (1967).

Webb et al; "Viruses in the Treatment of Cancer"; *The Lancet*; pp. 1206-1208 (Jun. 6, 1970).

Beverley et al; "Immune Responses in Mice to Tumour Challenge After Immunization with Newcastle Disease Virus-Infected or X-Irradiated Tumour Cells or Cell Fractions"; *Int. J. Cancer*; 11:212-223 (1973).

Bart et al; "Role of Interferon in the Anti-Melanoma Effects of Poly(I).Poly(C) and Newcastle Disease Virus"; *Nature New Biology*; 245 (147):229-230 (Oct. 24, 1973).

Eaton et al; "Autoimmunity Induced by Injection of Virus-Modified Cell Membrane Antigens in Syngeneic Mice"; *Infection and Immunity*; 15(1):322-328 (Jan. 1977).

Huang et al; "Studies on Viral Immunotherapy of Ascitic Tumors in Mice. I. Results of Treatment with Virus on Ehrlich and $S_{180}$ Ascitic Tumor Cells"; *Acta Academiae Medicinae Sinicae*; 6(3):213-216 (Jun. 1984).

Fenglan et al; "Studies on Combined Treatment of Cyclophosphamide and Virus in Mice Transplanted with S180 Ascitic Tumor Cells"; *Acta Academiae Medicinae Sinicae*; 7(5):376-379 (Oct. 1985).

Shoham et al; "Augmentation of Tumor Cell Immunogenicity by Viruses—An Approach to Specific Immunotherapy of Cancer"; *Nat. Immun. Cell Growth Regul*; 9:165-172 (1990).

Liebrich et al; "In Vito and Clinical Characterisation of a Newcastle Disease Virus-modified Autologous Tumour Cell Vaccine for Treatment of Colorectal Cancer Patients"; *Eur. J. Cancer*; 27(6):730-710 (1991).

Cassel et al; "A Ten-Year Follow-Up on Stage II Malignant Melanoma Patients Treated Postsurgically with Newcastle Disease Virus Oncolysate;" *Med. Oncol. & Tumor Pharmacother.*; 9(4):169-171 (1992).

Schirrmacher et al; "Modulation of Cancer Cell Immunogenicity by Viral Gene or Cytokine Gene Transfection and Clinical Application of Virus Modified Cancer Vaccines"; *Clinical & Experimental Metastasis*; vol. 10, Suppl. 1, p. 68 (Aug. 1992).

Sinkovics et al; "New Developments in the Virus Therapy of Cancer: A Historical Review"; *Intervirology*; 36:193-214 (1993).

Cassel et al; "Newcastle Disease virus as an antineoplastic agent"; *Cancer*; 18; pp. 863-868 (1965).

Kirn et al; "Replicating viruses as selective cancer therapeutics"; *Molecular Medicine Today*; pp. 519-527 (1996).

National Cancer Institute's complementary and alternative medicine (CAM) on NDV.

Reichard, K.W., et al; "Newcastle Disease Virus Selectively Kills Human Tumor Cells"; *Journal of Surgical Research*, vol. 52, pp. 448-453 (1992) XP 000674472.

Riechard, K.W., et al; "N-*myc* Oncogene Enhances the Sensitivity of Neuroblastoma to Killing by Newcastle disease Virus"; *Pediatric Surgery Surg.Forum*; vol. 43, pp. 603-606 (1992) XP 000674471.

Derwent, Database WPI Week 197632, *Thomson Scientific*, London, GB; AN 1976-60708X; "Drug for treatment of cancer—by culturing virus in hens egg or human embryo for two or three generations"; & JP 51 073117 A (Osaka Univ. Microbia) (Jun. 24, 1976) Abstract; XP 002301780.

Database Caplus; Chemical Abstracts Service, Columbus, OH; Zhang: "Attenuated Newcastle Disease Virus for Induction of Interferons to Combat Neoplasm or Viral Diseases"; (Sep. 4, 1991); XP 002915850.

Reichard, K.W., et al; "Retionic Acid Enhances Killing of Neuroblastoma Cells by Newcastle Disease Virus"; *Journal of Pediatric Surgery*, vol. 28, No. 10 (1993) XP 002032283.

\* cited by examiner

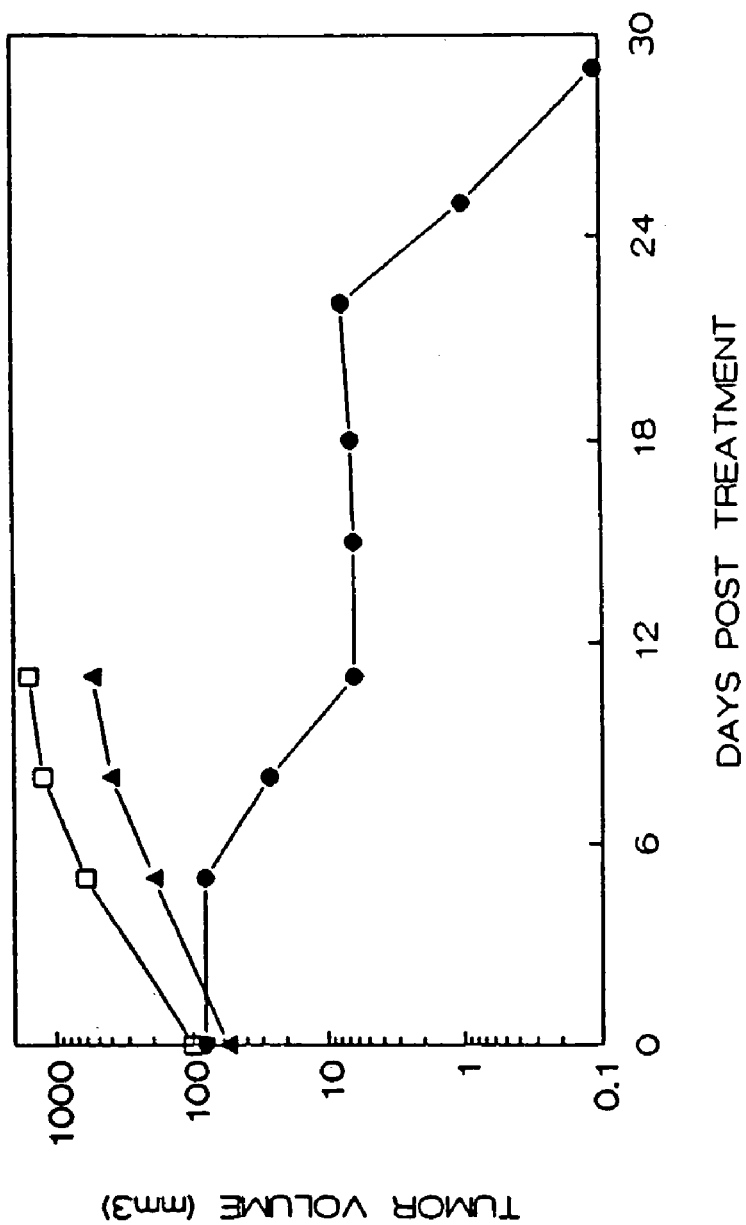
Fig. 1 IMR-32 Neuroblastoma Intralesional Therapy

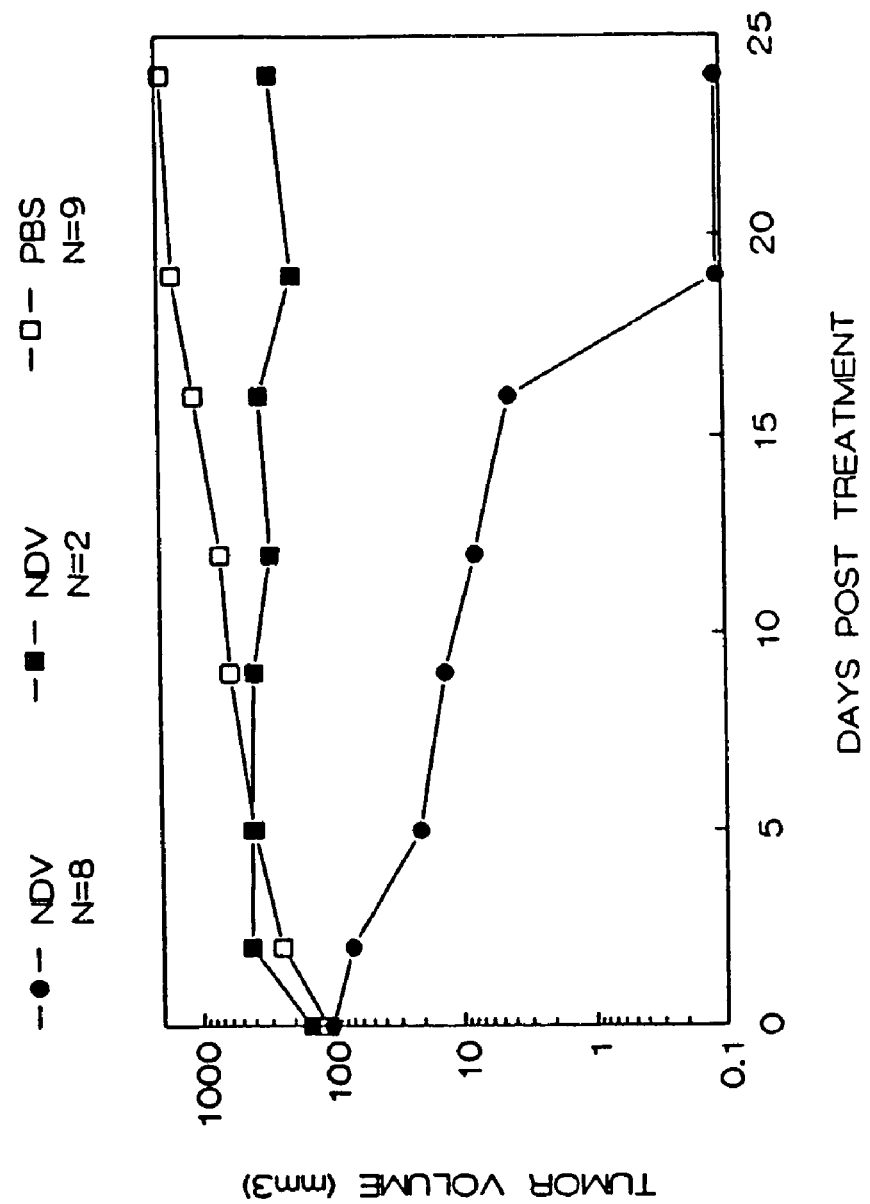
Fig. 2 HT1080 Fibrosarcoma Intralesional Therapy

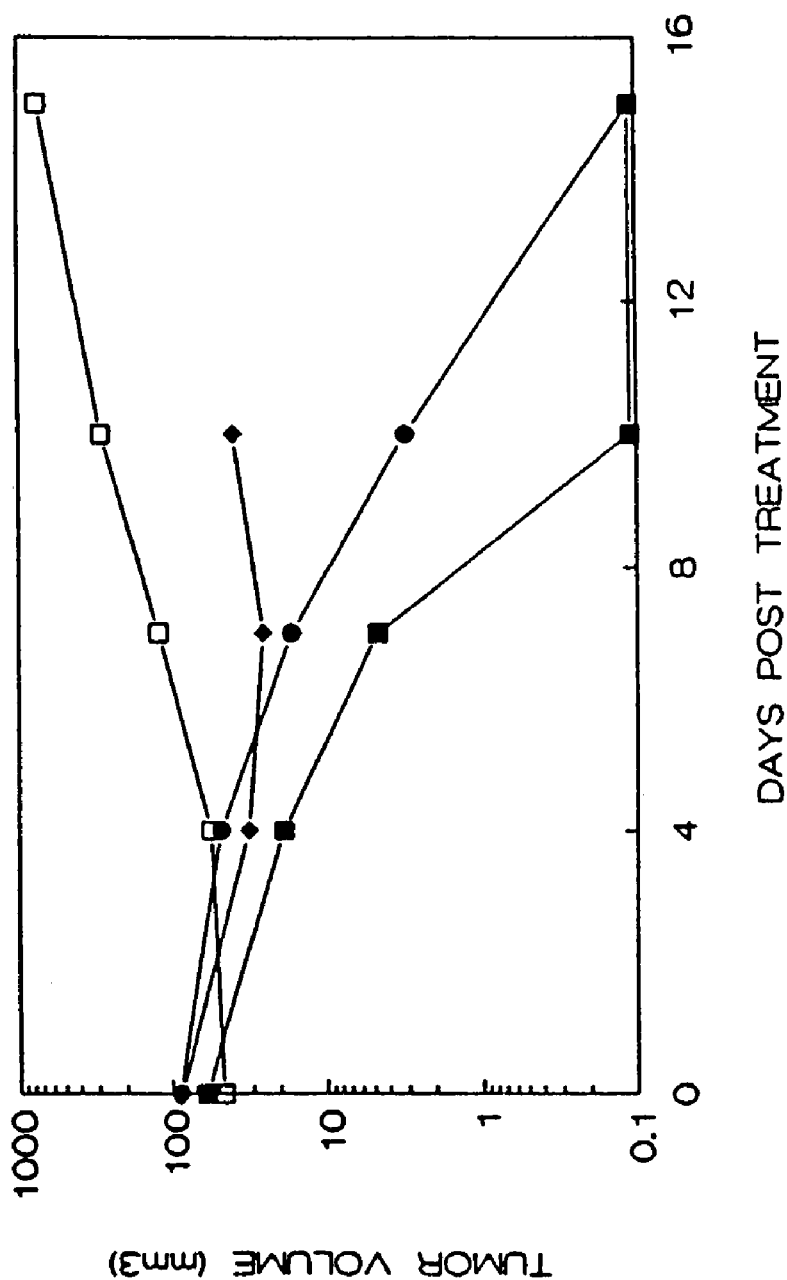
Fig. 3 Large Cell Lung Cancer: Intralesional Therapy

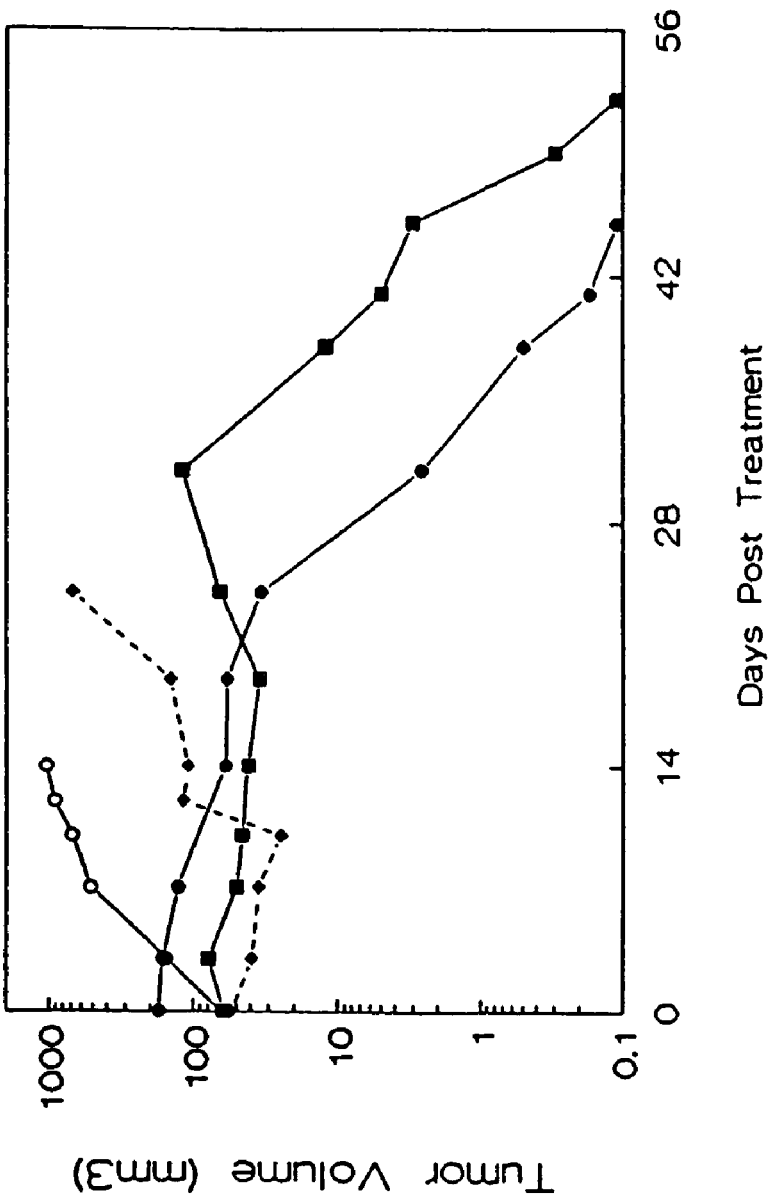
Fig. 4 IMR-32 Neuroblastoma Systemic Therapy

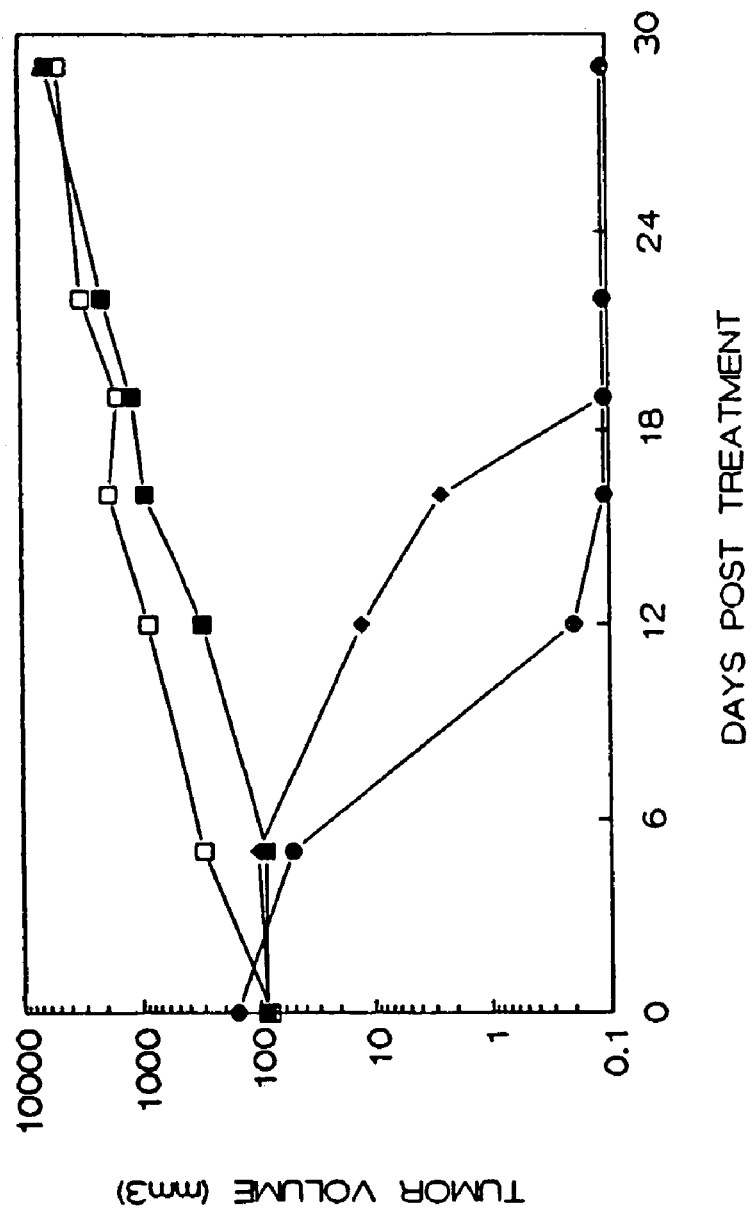

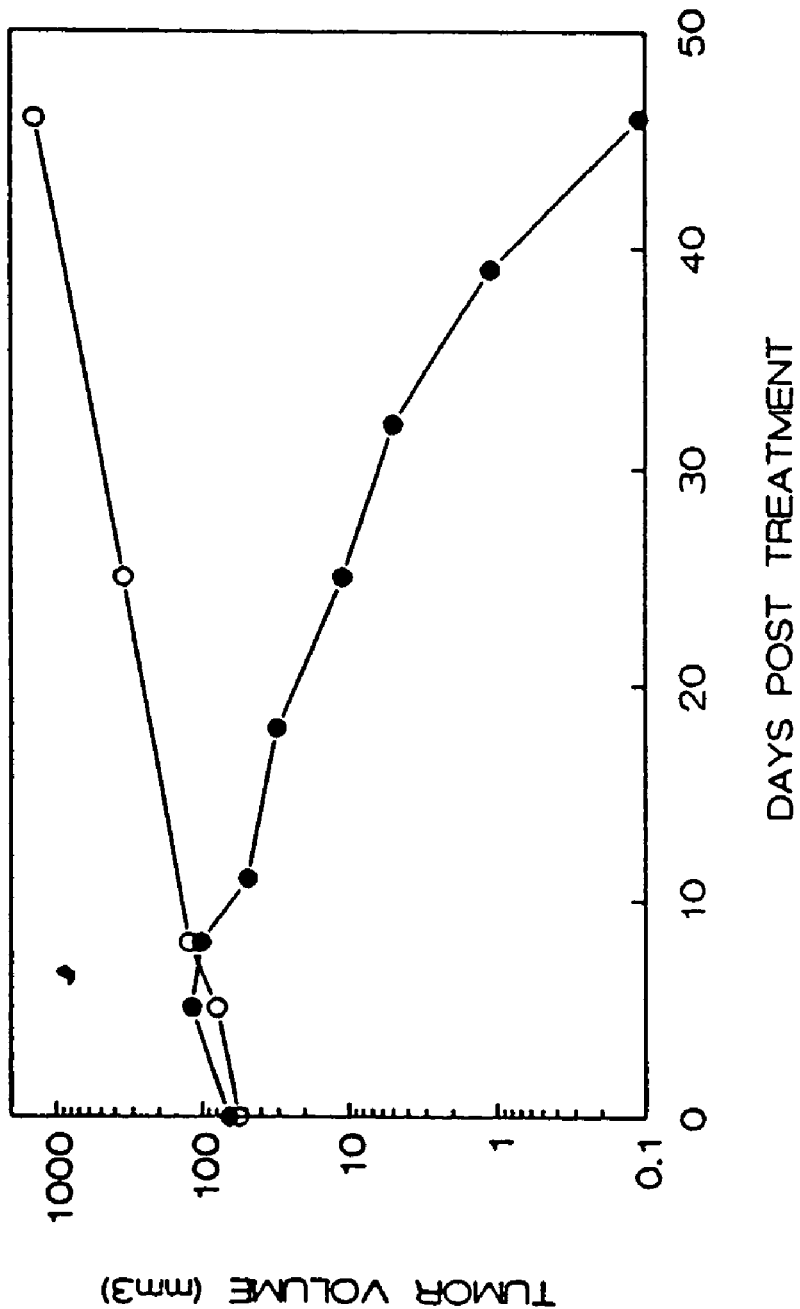

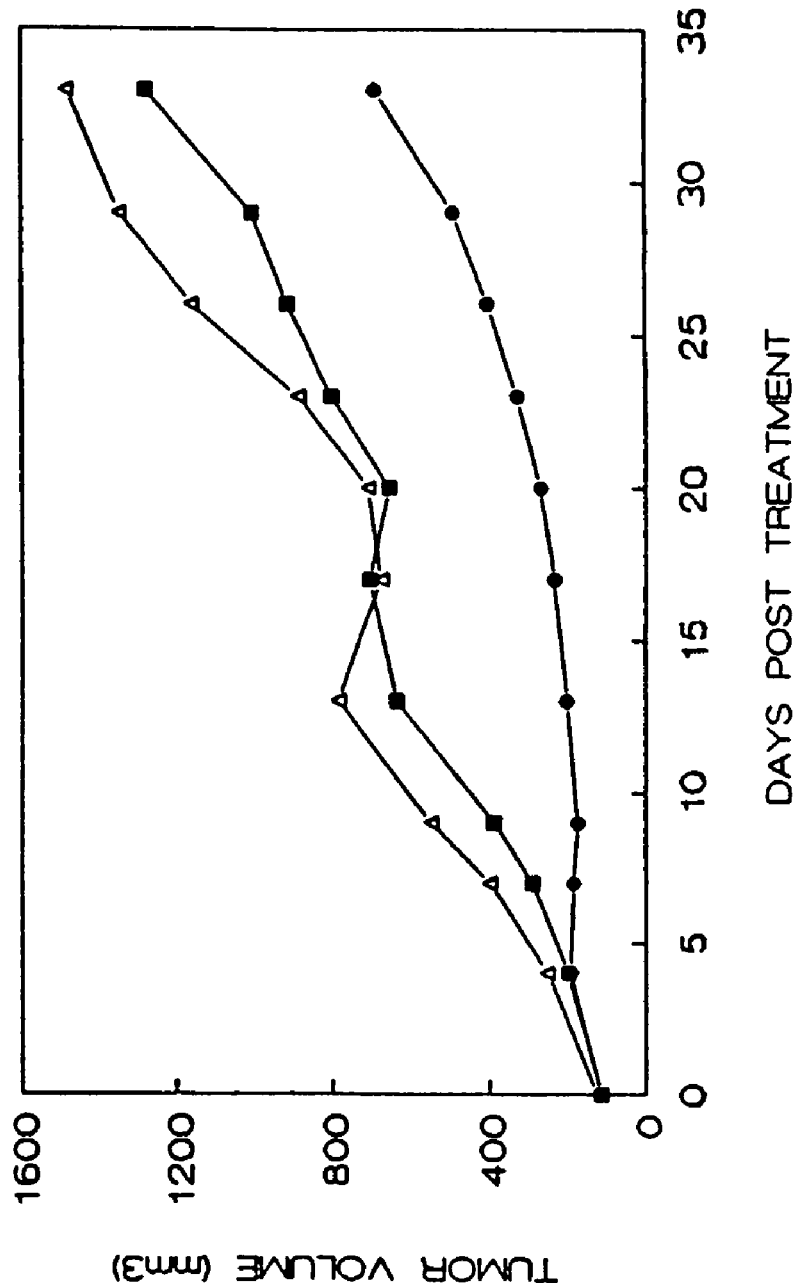
Fig. 7 KB8-5-11 Cervical Carcinoma Intralesional Therapy

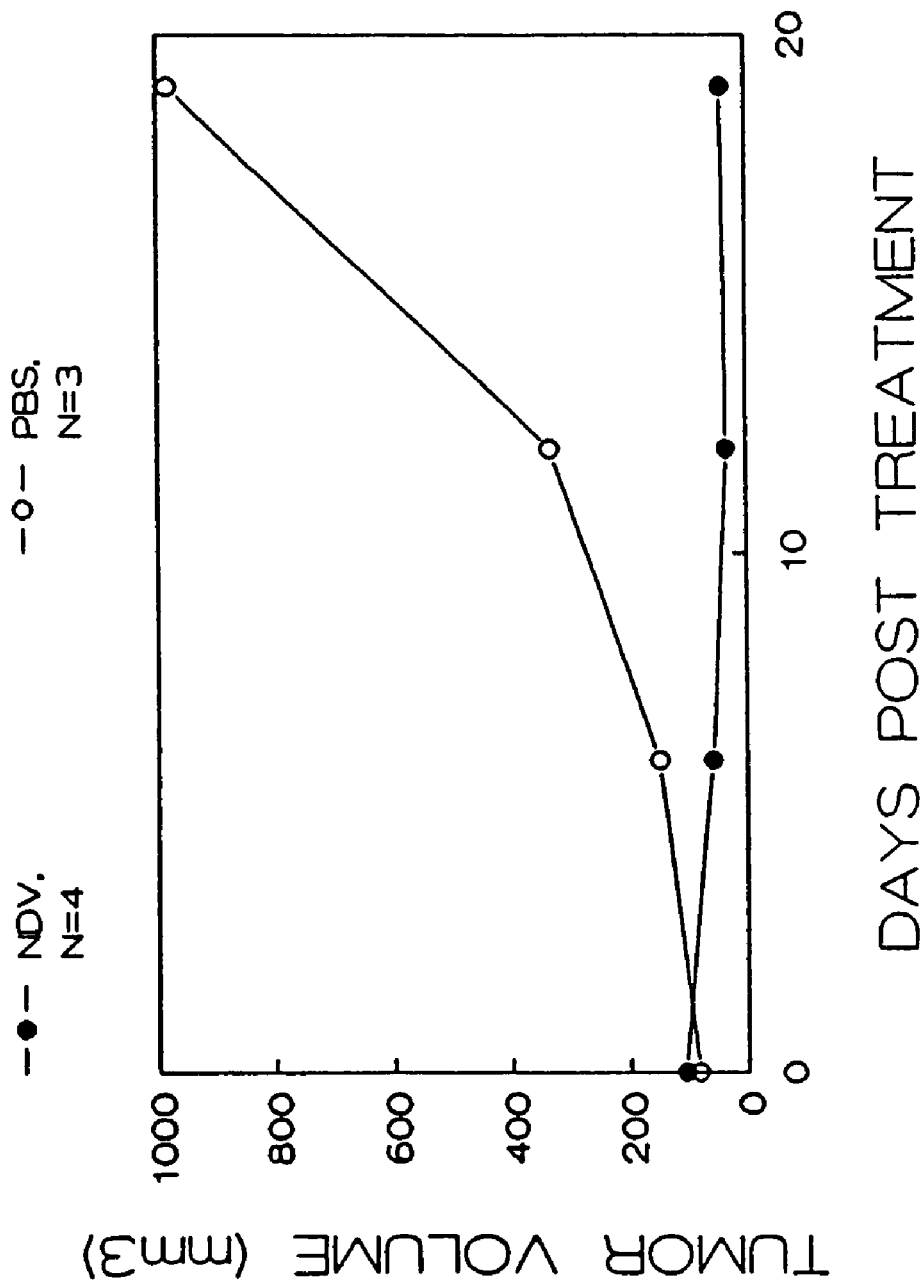
Fig. 8 PC-3 Prostate Carcinoma Intralesional Therapy

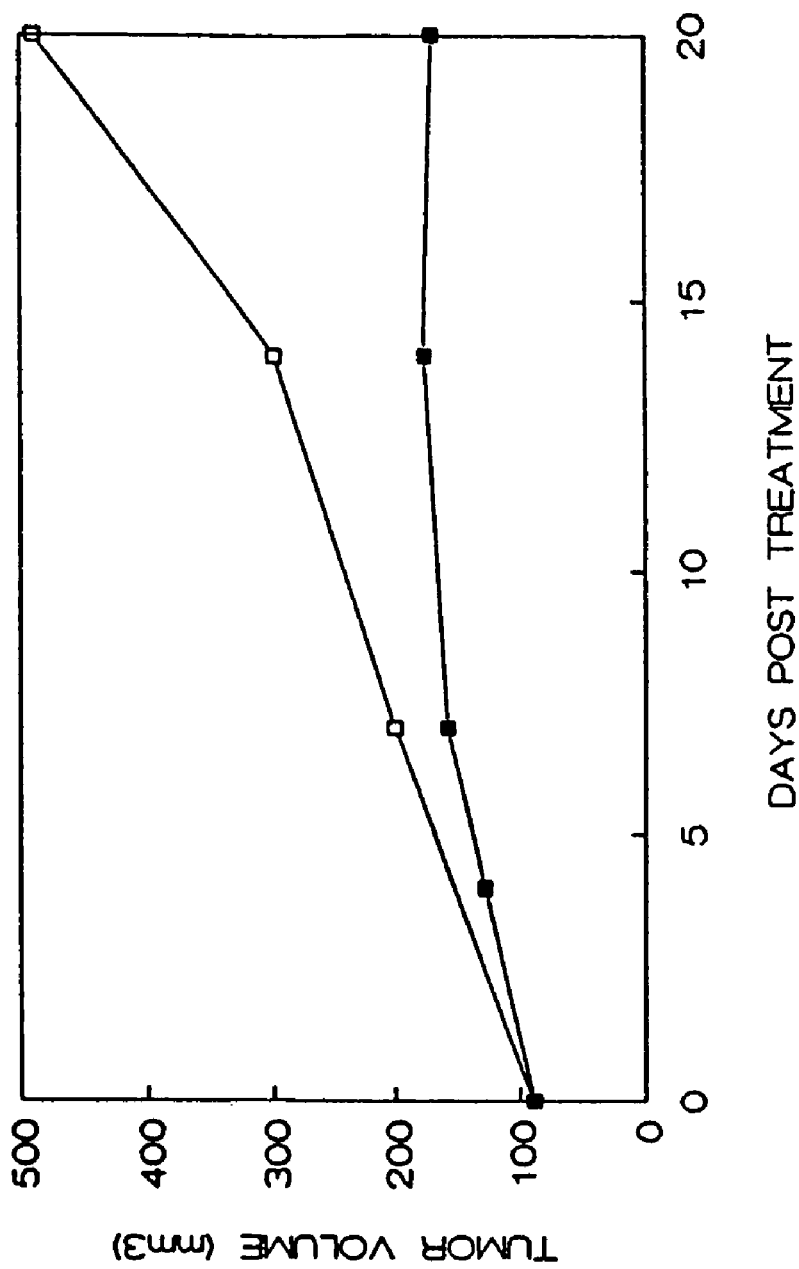
Fig. 9 HT29 Colon Carcinoma Intralesional Therapy

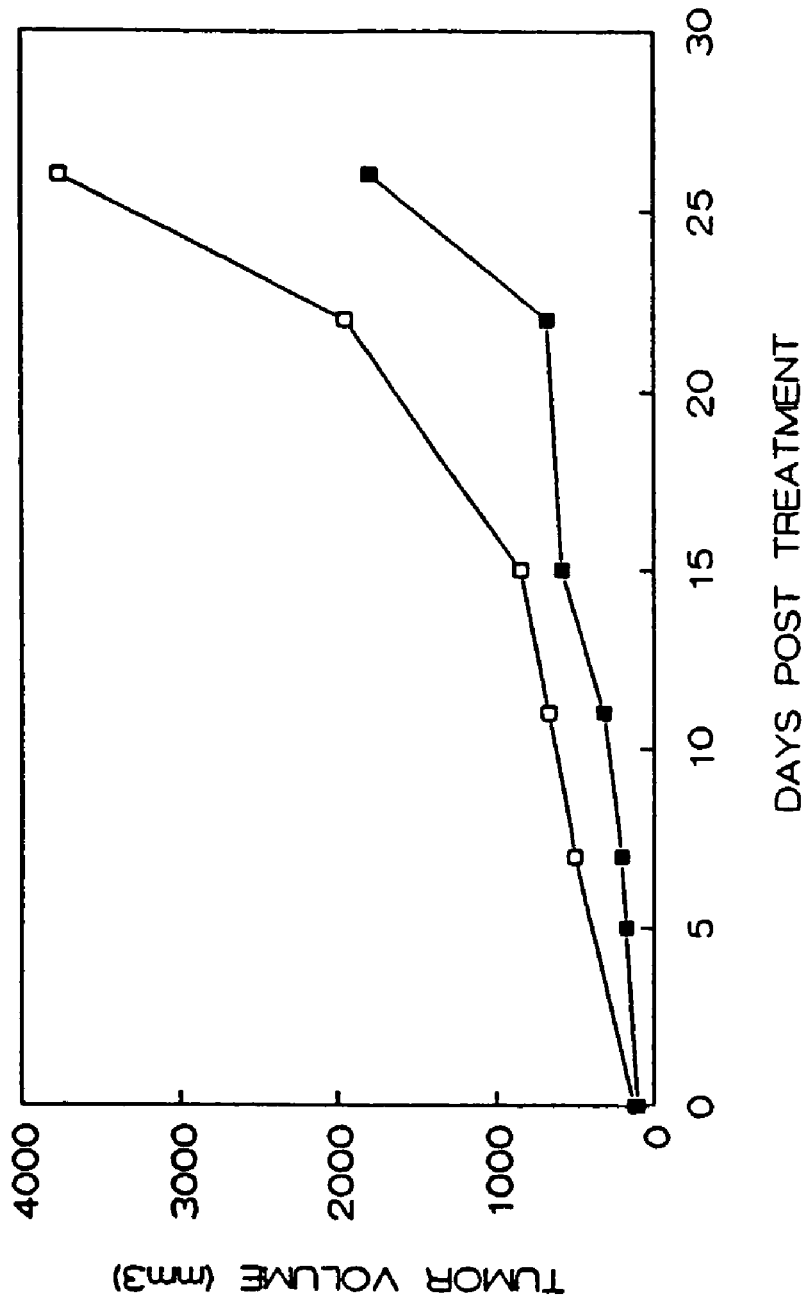
Fig. 10 SK-BR-3 Breast Carcinoma Intralesional Therapy

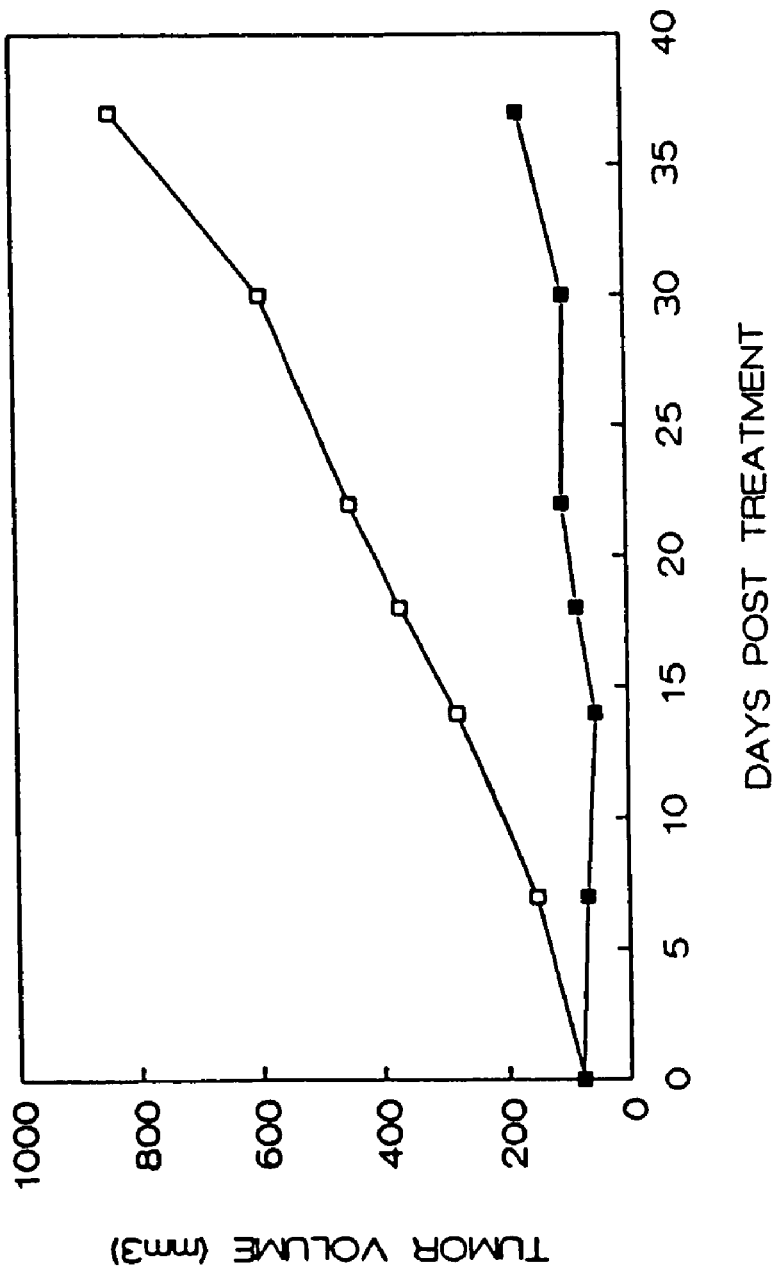
Fig. 11 SW620 Colon Carcinoma Intralesional Therapy

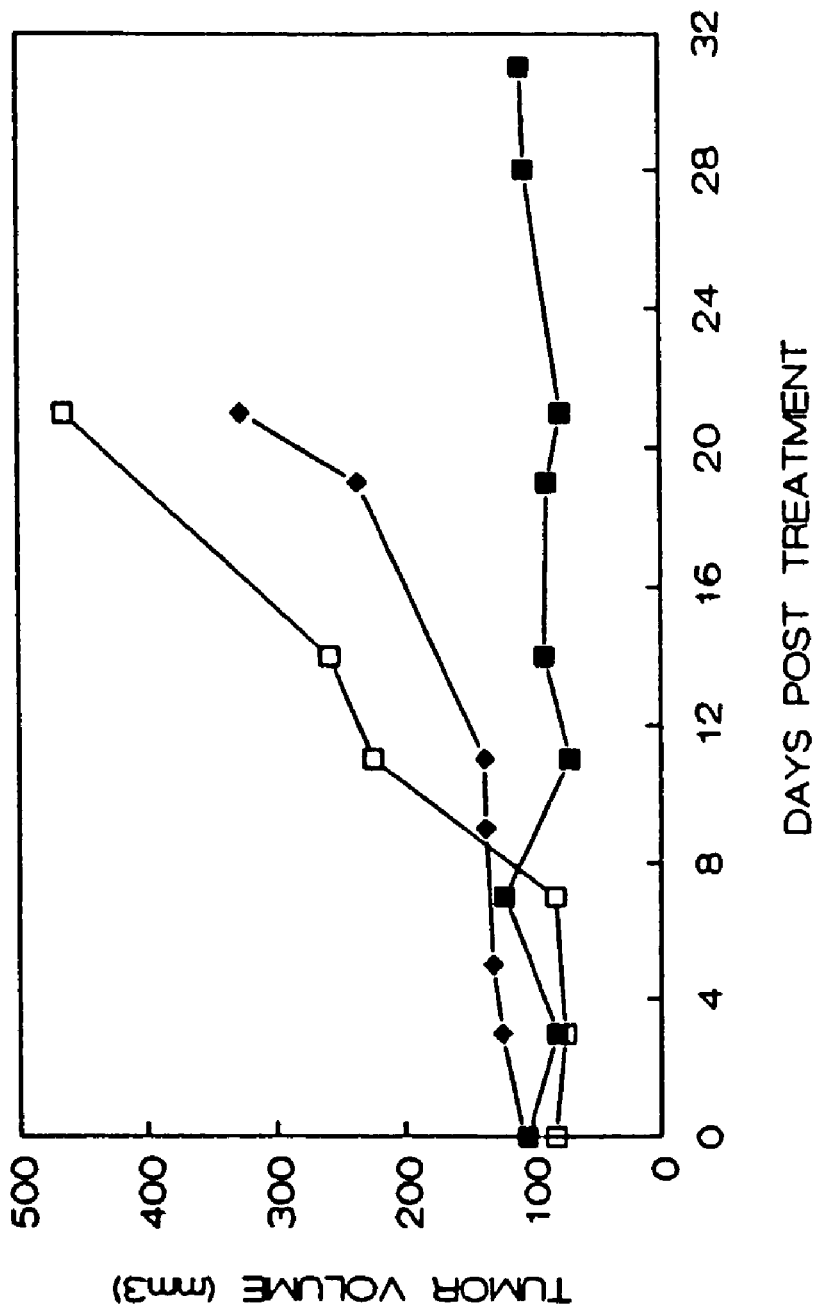
Fig. 12 MM17387 Colon Carcinoma Intralesional Therapy, 2nd Passage

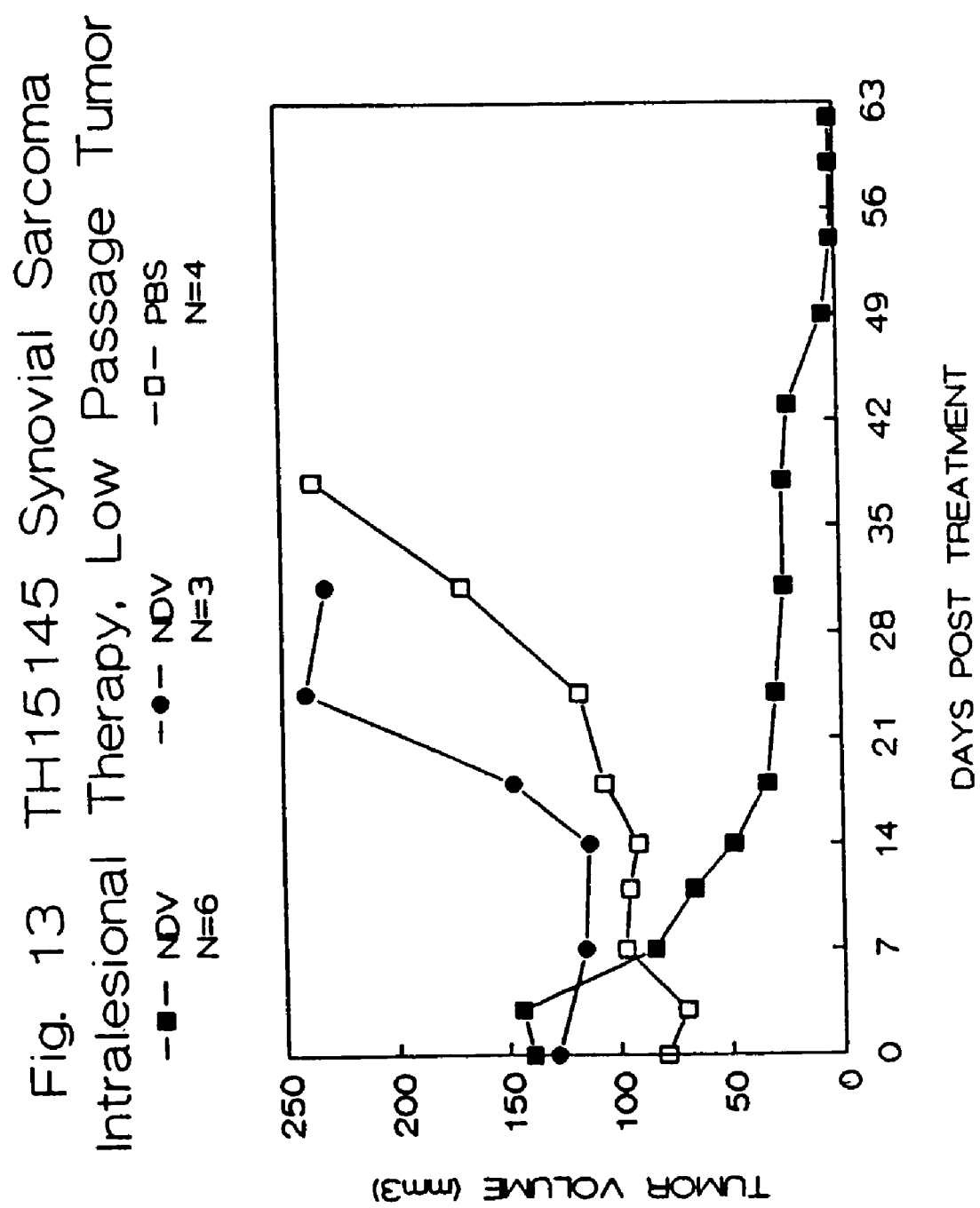
Fig. 13 TH15145 Synovial Sarcoma Intralesional Therapy, Low Passage Tumor

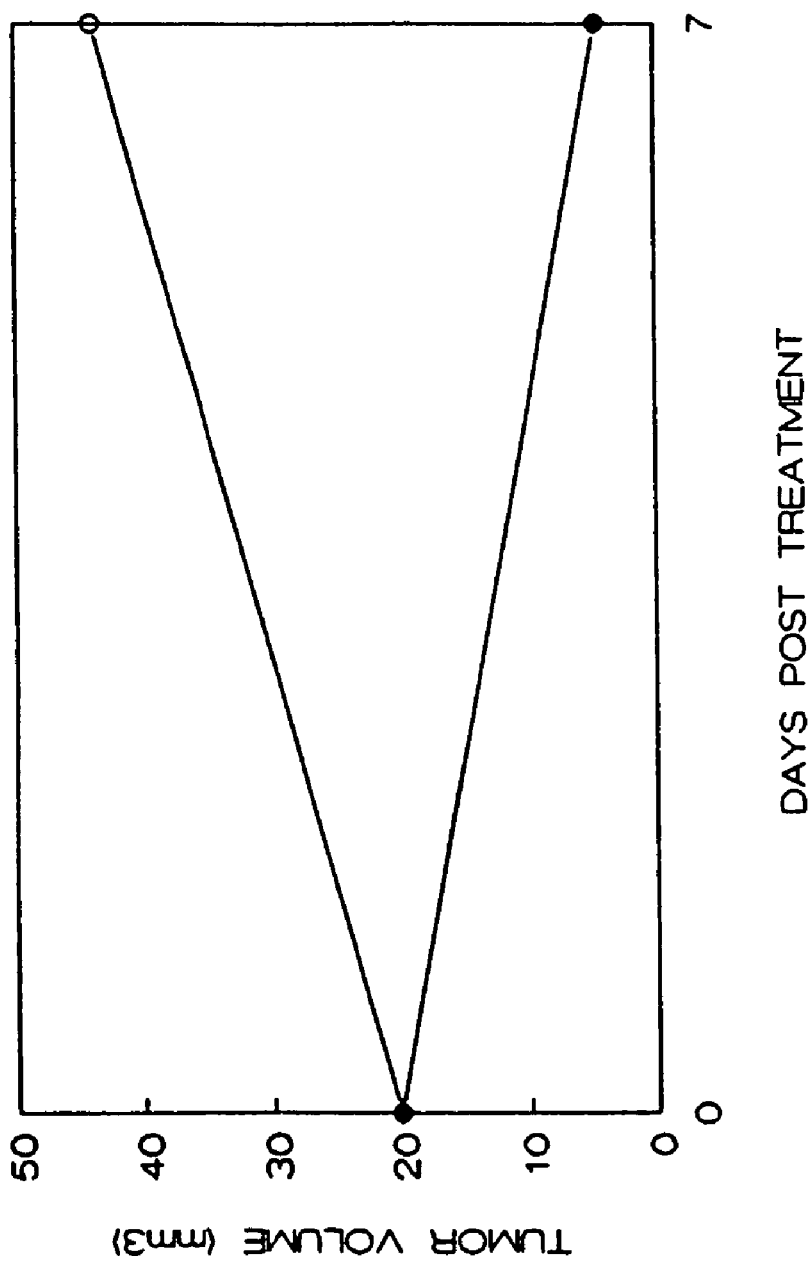
Fig. 14 MEL330 Melanoma Intralesional Therapy, 2nd Passage Tumor

METHODS OF TREATING AND DETECTING CANCER USING VIRUSES

RELATED APPLICATIONS

This application is a continuation of application Ser. No. 08/260,536, filed Jun. 16, 1994, now U.S. Pat. No. 7,056,689, which is a continuation-in-part of application Ser. No. 08/055,519, filed Apr. 30, 1993, now abandoned, the entire content of which is hereby incorporated by reference in this application.

This invention was made with government support under Grant No. RRO5477 awarded by the National Center for Research Resources. The government has certain rights in the invention.

FIELD OF THE INVENTION

The present invention relates generally to methods of treating and detecting cancer in mammals. More particularly, the invention relates to methods of treating and detecting cancer using certain viruses. The invention also relates to methods of producing viral compositions, to genetically engineered viruses containing heterologous nucleic acid and to kits containing the viral compositions and genetically engineered viruses.

BACKGROUND OF THE INVENTION

1. Cancer Treatment Despite recent advances in chemotherapy and radiation, cancer remains the second deadliest disease in the United States. There will be nearly two million new cancer cases diagnosed, and more than 525,000 people are expected to die from cancer in 1993. The overall five-year survival approximates fifty percent for all patients, and the prognosis remains particularly poor for those with advanced solid tumors.

2. Effect of Viruses on Cancer

An association between exposure to various viruses and tumor regression has been the subject of several previous case reports. Most of the viruses described in those reports are pathogenic in humans, and include mumps and measles. The effect of other specific viruses on particular types of cancer cells has also been described. Smith et al., (1956) *Cancer,* 9, 1211 (effect of APC virus on cervix carcinoma); Holzaepfel et al., (1957) *Cancer,* 10, 577 (effect of APC3 virus on epithelial tumor); Taylor et al., (1970) *J. Natl. Cancer Inst.,* 44, 515 (effect of bovine enterovirus-1 on Sarcoma-1); Shingu et al., (1991) *J. General Virology,* 72, 2031 (effect of bovine enterovirus, MZ-468, on F-647a leukemia cells); Suskind et al., (1957) *PSEBM,* 94, 309 (effect of Coxsackie B3 virus on HeLa tumor cells); Rukavishnikova et al., (1976) *Acta Virol.,* 20, 387 (effect of influenza A strain on ascites tumor).

The earliest references described partial tumor regression in patients treated with live attenuated viral vaccine with the aim to vaccinate them against smallpox or rabies. See DePace, N. G. (1912) *Ginecologia,* 9, 82-88; Salmon, P. & Baix (1922) *Compt. Rend. Soc. Biol.,* 86, 819-820. Partial regression of tumors and regression of leukemias have also been noted during naturally occurring measles infections. See Pasquinucci, G. (1971) *Lancet,* 1, 136; Gross, S. (1971) *Lancet,* 1, 397-398; Bluming, A. Z. and Ziegler, J. L. (1971) *Lancet,* 2, 105-106. In one study of 90 cancer patients intentionally infected with live mumps virus, partial tumor regression was noted in 79 cases. See Asada (1974) *Cancer,* 34, 1907-1928. Serious sequelae of infection with these human pathogens, however, is of major concern. Furthermore, the mechanism of any anti-cancer effect was never fully explored by the investigators. All of the effects noted upon exposure to those viruses were also temporary.

3. NDV Effect on Cancer

Newcastle Disease Virus ("NDV") is a member of the Paramyxovirus family. The natural hosts for NDV are chickens and other birds. NDV typically binds to certain molecules on the surface of animal host cells, fuses with the cell surface, and injects its genetic material into the host. Once inside, the viral genes direct the host cell to make copies of the virus. These copies of NDV are then released to infect other cells, which in turn destroy the host cell. Unlike some viruses, NDV is not known to cause any serious human disease. Unlike many other kinds of viruses (e.g., herpes, hepatitis, HIV), the Paramyxoviruses do not interfere with the host cell genes, and are not known to be carcinogenic.

Temporary regression of tumors has been reported in a small number of patients exposed to NDV, all of whom eventually succumbed to their cancers. See, Csatary, L. K. (1971) *Lancet,* 2, 825. Csatary noted the regression of a gastrointestinal cancer in a chicken farmer during an epidemic of Newcastle disease in his chickens. In a similar anecdotal report, Cassel, W. A. and Garrett, R. E. (1965) *Cancer,* 18, 863-868, noted regression of primary cervical cancer, which had spread to the lymph nodes, in a patient following injection of NDV into the cervical tumor. Since the mechanism of the observed tumoricidal activity was thought to be immunologic, no work was carried out to address direct tumor cytotoxicity of the virus. Instead, efforts focused upon the immuno-modulating effects of NDV. See, for example, Murray, D. R., Cassel, W. A., Torbin, A. H., Olkowski, Z. L., & Moore, M. E. (1977) *Cancer,* 40, 680; Cassel, W. A., Murray, D. R., & Phillips, H. S. (1983) *Cancer,* 52, 856; Bohle, W., Schlag, P., Liebrich, W., Hohenberger, P., Manasterski, M., Möller, P., and Schirrmacher, V. (1990) *Cancer,* 66, 1517-1523.

4. Delivery of Genes to Cancer Cells

Current approaches for delivery of genetic material into cells include the use of retrovirus vectors. See, e.g., Miller et al., (1992) *Nature,* 357, 455. The retrovirus delivers negatively-stranded RNA and the reverse transcriptase enzyme to produce a positive strand DNA. There are disadvantages in using retroviruses because the viruses are rendered incapable of producing progeny viruses, i.e., virus amplification cannot take place. Also, the use of retroviruses to deliver genetic material to cancer cells is not desirable because retroviral vectors tend to infect tumor cells at a relatively low percentage, thereby precluding efficient in-situ transfer of the desired genetic material into the tumor site. Furthermore, production of the gene of interest delivered by the retrovirus occurs at a rate determined by the cell cycle of the host cell which can severely limit the amount of gene product being translated.

The use of certain other viruses as recombinant vehicles for expression of genetic material has been described, for instance, vaccinia [Ramshaw et al., (1992) *Immunological Reviews,* 127, 157], adenovirus [Bett et al., (1993) *J. Virology,* 67, 5911; Natuk et al., (1992) *Proc. Natl. Acad. Sci.,* 89, 7777; Chengalvala at al., *Vaccine,* 9, 485; Berkner, (1988) *BioTechniques,* 6, 616], and influenza virus [Li et al., *Proc. Natl. Acad. Sci.,* 90, 5214]. See also, generally, Lyerly et al., (1993) *Arch. Surg.,* 128, 1197.

SUMMARY OF THE INVENTION

The invention provides a method of treating cancer in a mammal comprising administering to the mammal an effective amount of virus in a pharmaceutically-acceptable carrier.

In one embodiment, the virus is a Paramyxovirus. In a preferred embodiment, the virus is Newcastle Disease Virus.

The invention also provides a method of treating cancer in a mammal comprising administering to the mammal Paramyxovirus in combination with another agent, both being administered in amounts sufficient so that the combination is effective against the cancer.

The invention further provides methods for producing viral compositions that may be used in the treatment or detection of cancer. The methods comprise cultivating virus, preferably Paramyxovirus, in vitro in a mammalian cell culture.

The invention further provides methods of detecting cancer cells in a mammal. In one embodiment, Newcastle Disease Virus is employed as an imaging agent. To do so, labeled Newcastle Disease Virus may be administered and detected in the mammal. Alternatively, a labeled component that binds to Newcastle Disease Virus may be administered, and detected in the mammal. In another embodiment, Newcastle Disease Virus is administered to the mammal, and subsequently measured. The quantity of the virus measured in the body fluid or tissue of the mammal is an indication of the presence of cancer cells.

The invention also provides a genetically engineered Paramyxovirus comprising heterologous nucleic acid encoding a biologically or chemically active peptide, polypeptide or protein. The heterologous nucleic acid is operatively linked to one or more control sequences.

The invention further provides an article of manufacture and kit containing materials useful for treating and detecting cancer. The article of manufacture comprises a container, a label on the container, and a composition contained within the container, the composition being effective for treating and detecting cancer, and the label on the container indicating that the composition can be used for treating and detecting cancer. The active agent in the composition comprises Newcastle Disease Virus. The kit comprises the container holding the composition effective for treating and detecting cancer, as well as other compositions, such as buffers, diluents, and syringes.

BRIEF DESCRIPTION OF THE DRAWINGS

FIG. 1 illustrates the regression of IMR-32 human neuroblastoma xenografts in athymic mice following intra-tumor injection with live NDV (strain 73-T)

FIG. 2 shows regression of HT-1080 human fibrosarcoma xenografts in athymic mice following intra-tumor injection with live NDV (strain 73-T).

FIG. 3 shows regression of NCI-H460 human large cell lung carcinoma xenografts in athymic mice following intra-tumor injection with live NDV (strain 73-T).

FIG. 4 shows regression of IMR-32 human neuroblastoma xenografts following systemic (intraperitoneal) injections of live NDV (strain 73-T).

FIG. 5 illustrates the effectiveness of a strain (M, Mass MK107) of NDV of relatively moderate virulence with that of a strain of relatively high virulence (73-T) in causing tumor regression.

FIG. 6 shows regression of U87MG human glioblastoma xenografts in athymic mice following intra-tumor injections with live NDV (strain 73-T).

FIG. 7 shows growth inhibition of KB8-5-11 human cervical carcinoma in athymic mice following intra-tumor injections with live NDV (strain 73-T).

FIG. 8 shows regression of PC-3 human prostate carcinoma in athymic mice following intratumor injections with live NDV (strain 73-T).

FIG. 9 shows growth inhibition of HT29 human colon carcinoma in athymic mice following intra-tumor injections with live NDV (strain 73-T).

FIG. 10 shows growth inhibition of SK-BR-3 human breast carcinoma in athymic mice following intra-tumor injections with live NDV (strain 73-T).

FIG. 11 shows growth inhibition of SW620 human colon carcinoma in athymic mice following intra-tumor injections with live NDV (strain 73-T).

FIG. 12 shows growth inhibition of MM17387 human colon carcinoma in athymic mice following intra-tumor injections with live NDV (strain 73-T).

FIG. 13 shows regression of TH15145 human synovial sarcoma in athymic mice following intra-tumor injections with live NDV (strain 73-T).

FIG. 14 shows regression of a MEL330 human melanoma xenograft in athymic mice following intra-tumor injections with live NDV (strain 73-T).

DETAILED DESCRIPTION OF THE PRESENTLY PREFERRED EMBODIMENTS

The present invention provides methods for treating mammalian cancer using certain viruses. In one embodiment of the invention, the virus is a Paramyxovirus. Paramyxoviruses useful in the practice of the present invention are preferably capable of specifically distinguishing mammalian cancer cells from normal mammalian cells. The Paramyxoviruses of the invention are also preferably cytolytic viruses. In an even more preferred embodiment of the invention, the cytolytic Paramyxovirus is a Newcastle Disease Virus ("NDV"). As used in the present application, the terms "virus," "Paramyxovirus," and "Newcastle Disease Virus" are employed in a broad sense and refer to both intact viruses and viral fragments, as well as genetically, physically or chemically modified viruses and viral fragments.

Paramyxoviruses, including various strains of NDV, both cytolytic and non-cytolytic, are publicly available, and may be obtained from vendors such as the American Type Culture Collection (ATCC), Rockville, Md.

The virus employed in the invention may be prepared by a variety of methods. For example, NDV may be prepared in 8 to 10 day old fertilized chicken eggs (obtained from SPAFAS, Inc., Roanoke, Ill.). Methods of isolating the virus are known in the art and are described, for example, by Weiss, S. R. & Bratt, M. A. (1974) J. Virol, 13, 1220-1230. This method is further described in Example #1 below. Using this isolation method, NDV may be obtained which is about 90-95% pure.

Alternatively, the virus may be prepared in an in vitro cell culture. Preferably, the cell culture comprises mammalian cells, and more preferably, mammalian cancer cells. One advantage of using this method of preparing the virus is that it avoids problems associated with residual foreign proteins in the viral preparation. Mammalian cells contemplated by these methods include but are not limited to, human fetal fibroblasts and established cell lines such as HT1080 human fibrosarcoma (publicly available from ATCC) or the patient's own cancer cells. The cells may be anchorage-dependent or anchorage-independent.

Cell culture techniques that may be employed in the virus preparation are known in the art and may include use of stationary culture flasks with large surface areas or roller-type flasks. Preferably, the type of culture system selected can support relatively large numbers of cells.

Cell culture mediums that can be employed in the virus production are known to those skilled in the art. The medium typically includes a nutrient source, antibiotic(s) and albumin or a serum source that contains growth factor(s). It is within the skill in the art to select particular mediums and medium constituents suitable for the cells employed in the culture.

An example of a suitable culture medium for cultivating NDV in an in vitro cell culture is shown below in Table 1:

| Reagent | Source | Amount |
|---|---|---|
| Opti-MEM | Gibco BRL Grand Island, NY | 500 ml |
| Fetal Bovine Serum | Gibco BRL Grand Island, NY | 50 ml |
| MEM Non-essential Amino Acids (100X), 10 mM | Gibco BRL Grand Island, NY | 5 ml |
| Antibiotic-Antimycotic (100X), contains 10,000 units penicillin, 10,000 µg streptomycin and 25 µg amphotericin B per ml | Gibco BRL Grand Island, NY | 5 ml |
| Glutamine, (100X) 200 mM | Gibco BRL Grand Island, NY | 5 ml |

Culture conditions typically include incubation at a desired temperature (such as 37° C.), as well as selected concentrations of oxygen and carbon dioxide. The particular culture conditions selected can be determined in accordance with the cells employed in the culture, and determination of such conditions is within the skill in the art.

The cells are placed in the culture vessel and allowed to incubate and grow under the selected culture conditions. Preferably, anchorage-dependent cells are allowed to grow to confluence or peak growth. The time required for growth will vary depending upon the size of the initial cell inoculum added to the culture vessel and doubling time of the cell line being employed. Preferably, about $3 \times 10^3$ to about $3 \times 10^5$ cells are plated per $cm^2$ and grown for one to five days. For virus inoculation of the cell culture, the medium is removed from the cells (for adherent cells, by aspiration of the culture medium; for cells grown in suspension, by centrifugation of the cell suspension and aspiration of the cell supernatant) and the virus (after reconstitution) is added to the cells in a minimal volume of medium or saline solution (such as Hank's Balanced Salt Solution, Gibco) to prevent dehydration. Preferably, this volume ranges from about 10 to about 2500 microliter per $cm^2$ culture vessel surface area or $10^5$ cells. The preferred dilution of virus inoculum ranges from about 0.001 to about 10 infectious units per cell, the optimal ratio depending on the particular virus and cell line. The virus is then grown from about 1 to 7 days, the length of time being primarily determined by the residual survival of the cell line. For NDV, the optimal time of harvest is 1 to 5 days after virus inoculation.

The virus can then be harvested by either removing the supernatant and replacing it with fresh medium or fresh medium with fresh cells at 12 to 48 hour intervals or freeze-thawing the cells to release virus in the supernatant. The supernatant can then be centrifuged and ultracentrifuged to recover the virus in relatively pure form. The purity of the viral preparation may be tested by protein determination and/or by electrophoresis. The virus can then be added to a pharmaceutically-acceptable carrier, described further below.

In accordance with a first method of treating cancer in a mammal, an effective amount of virus is administered to the mammal. The term "cancer" in the present invention is used in a broad sense and refers to the physiological condition in mammals that is usually characterized by unregulated cell growth. In one embodiment of the method, Paramyxovirus, preferably, NDV, is administered to the mammal. It is contemplated that such viruses may be used to treat a variety of cancers, including but not limited to lung carcinoma, breast carcinoma, prostate carcinoma, colon adenocarcinoma, cervical carcinoma, endometrial carcinoma, ovarian carcinoma, bladder carcinoma, Wilm's tumor, fibrosarcoma, osteosarcoma, melanoma, synovial sarcoma, neuroblastoma, and glioblastoma. The virus may be administered to the mammal at any time during the course of malignant disease when cancer is detected to reduce primary tumor burden or progression as well as to reduce metastasis. Alternatively, the virus may be administered as a prophylactic measure, prior to the onset or detection of cancer in the mammal. It is also contemplated that the virus may be administered to a mammal already treated for cancer if that cancer fails to completely respond or recurs. Preferably, if a tumor is operable, the virus is administered after the bulk of the tumor has been surgically removed.

Although not fully understood, it is believed that NDV has direct cytolytic activity on the cancer cells. It is also believed that NDV is capable of specifically differentiating cancer cells from normal, healthy cells. Results (not shown) have indicated that several oncogenes (H-ras, N-ras, and N-myc) which are known to confer malignant behavior to cancer cells, enhance the susceptibility of cells to killing by NDV. See, Lorence, R. M., Reichard, K. W., Cascino, C. J. et al. (1992) *Proc. Am. Assoc. Cancer Res.,* 33, 398; Reichard, K. W., Lorence, R. M., Cascino, C. J., et al. (1992) *Surg. Forum,* 43, 603-606. In addition, it has been observed that treatment of cells with retinoic acid (vitamin A) also enhances lysis of cancer cells by NDV. Reichard, K. W., Lorence, R. M., Katubig, B. B., et al. (1993) *J. Pediatr. Surg.,* 28, 1221.

Cytolytic activity by NDV is believed to be the result of direct binding of the virus to the cancer cell. A component of the cell surface molecule(s) allowing NDV binding to chicken cells has been identified. See, Paulson, J. C., Sadler, J. E. & Hill, R. C. (1979) *J. Biol. Chem.,* 254, 2120-2124. The molecule appears to be relatively complex glycoprotein(s) and/or glycolipid molecule(s) on which sialic acid components are arranged in a particular configuration. It is the Applicants' present belief that the variations in sialic acid-containing glycoproteins and/or glycolipids on the surface of cancer cells may mediate NDV's specificity and activity. For instance, sensitivity of cancer cells to NDV has been shown to be diminished by pre-treatment with neuramimidase which cleaves off the sialic acid residues. See, Reichard, K. W., Lorence, R. M., Katubig, B. B., et al. (1993) *J. Pediatr. Surg.,* 28, 1221.

The virus may be administered to the mammal in a pharmaceutically-acceptable carrier. Pharmaceutically-acceptable carriers are well known to persons skilled in the art. For instance, suitable carriers for administering the virus may include fluids such as water, saline, buffer, and cell culture medium. More preferably, a saline solution is used as the carrier. It will be apparent to those persons skilled in the art that certain carriers may be more preferable depending upon, for instance, the route of administration and concentration of virus being administered.

The virus is preferably administered to the mammal by injection (e.g., intravenous, intralesional, intraperitoneal, subcutaneous, intramuscular or endoscopic). The virus can be administered either directly at the tumor site by local or regional injection, or systemically. Alternatively, the virus may be administered by routes including but not limited to intranasal, oral, rectal or topical application. Effective dosages and schedules for administering the virus may be determined empirically, and making such determinations is within the skill of the art. Applicants have found local treatment doses in the range of about $4 \times 10^8$ to about $4 \times 10^{10}$ PFU of NDV per kilogram of body weight of the mammal to be particularly effective for treating tumors. For systemic treatment, Applicants believe that a range from about $4 \times 10^{10}$ to about $4 \times 10^{12}$ PFU per kilogram may be preferable in treating cancer. It is understood by those skilled in the art that the dose of virus that must be administered will vary depending on, for example, the mammal which will receive the virus, the type of cancer, the extent of cancer cell growth or metastasis, the biological site or body compartment of the tumor(s), the strain of virus, the route of administration, and the identity of any other drugs or treatment being administered to the mammal, such as radiation, chemotherapy, or surgical treatment. It is also understood that it may be necessary to give more than one dose of the virus. The optimal interval between such multiple doses of virus can be determined empirically and is within the skill of the art. Administration of the virus should be continued until health has been restored to the mammal.

In accordance with another method of treating cancer in a mammal, an effective amount of virus is administered to the mammal in combination with another agent. In a preferred method, an effective amount of NDV is administered in combination with another agent. The virus may be administered to the mammal as described above. The other agent administered in combination with the virus may be a naturally-occurring or a synthetic substance, and preferably has anti-cancer activity, immune-enhancing activity, or virus-enhancing activity.

In one embodiment of the method, the agent is a cytotoxic or cytostatic agent. The cytotoxic or cytostatic agent may be a chemotherapeutic compound known in the art. Chemotherapeutic compounds contemplated by the present invention include, but are not limited to Thiotepa, Busulfan, Cyclophosphamide, Methotrexate, Cytarabine, Bleomycin, Cisplatin, Doxorubicin, Meiphalan, Mercaptopurine, Vinblastine, 5-Fluorouracil, Taxol (paclitaxel), and Retinoid Acid. Typically, cytotoxic or cytostatic agents function in destroying cells and/or inhibiting their multiplication and are thus, useful in treating cancer.

In another embodiment of the method, the agent is an antibody. The antibody may be a naturally occurring antibody or an antibody modified biologically, chemically, physically, or genetically using methods which are within the skill of the art. Such antibodies may enhance the anti-cancer activity of the virus by binding to the tumor cell or to the virus after it is bound to the tumor cell.

In another embodiment of the method, the agent is an immune-enhancing agent such as an immunoadjuvant or cytokine. Immunoadjuvants and cytokines, also referred to as "biological response modifiers," are known in the art. Generally, such molecules are useful in stimulating or enhancing host defense mechanisms and are therefore useful in anti-cancer therapy. Examples of immunoadjuvants or cytokines that may be administered include, but are not limited to interferon(s), colony stimulating factor (CSF), tumor necrosis factor (TNF), growth factors, and interleukins such as IL-1, IL-2, and IL-6.

In another embodiment of the method, the agent is an immunosuppressive agent. Preferably, the immunosuppressive agent is a pharmaceutical compound known in the art. Immunosuppressive agents contemplated by the present invention include, but are not limited to Cyclosporin A, Azathiaprine, and Leflunomide and various corticosteroid preparations. Immunosuppressive agents are believed to function by blocking the immune response (cell-mediated, antibody-mediated, and cytokine-mediated) against viruses which may enhance the anti-cancer activity of the virus.

The agent is preferably administered in a pharmaceutically-acceptable carrier such as water, saline, or buffer. Modes of administration of the agent to the mammal include but are not limited to oral administration or injection (e.g., intravenous, intraperitoneal, subcutaneous, intramuscular). It is within the skill in the art to determine acceptable carriers and proper means of administering the agent. The Paramyxovirus and the agent may be administered by the same means or by different means. For instance, the virus may be administered to the mammal by intravenous injection while the other agent is administered orally to the mammal.

The virus and agent may also be encapsulated in a liposome or other pharmaceutically-acceptable sac-like structure. Alternatively, the virus and the agent may be coupled by conjugation or linking techniques known in the art. The agent may be incorporated within the virus, the viral genome, or viral proteins using molecular genetics techniques, as described in further detail below.

Effective dosages and schedules for administering the virus are described above. Effective dosages and schedules for administering the other agent in combination with the virus may be determined empirically, and making such determinations is within the skill of the art. Prior to administering the virus and the other agent, it is preferable to determine toxicity levels of all components so as to avoid deleterious effects. Depending on the agent administered, the virus and the agent may have additive or synergistic activity. For instance, administration of the virus may reduce the effective dosage required of the other agent. It will be understood by those persons skilled in the art that the dose of the other agent administered will vary, depending on, for example, the mammal being treated, the type of cancer, the systemic location of the cancer, and the amount of virus being administered to the mammal. It is possible that multiple doses of the other agent must be administered in combination with the virus. The agent may be administered at time intervals different from the virus administration. Intervals of the administration can be determined empirically, and such determination is within the skill of the art. Administration of the virus and the agent should be continued until health has been restored to the mammal.

The invention also relates to a method of detecting cancer cells in a mammal using Paramyxovirus as an imaging agent. It is believed that such imaging may assist not only in diagnosis and detection, but may also guide further therapy such as surgery. In a preferred method, NDV is used as the imaging agent. To detect the cancer cells, the virus can be administered as described above. The virus then localizes to the cancer cell sites and binds to the cancer cells.

In one embodiment, labeled virus may be administered to the mammal. Labels useful in the method are well known in the art and include but are not limited to, enzymes, fluorophores, radioisotopes, and biotin-avidin. It is contemplated that radioisotopes such as Indium-ill having relatively short half lives will be preferred labels. The labels can then be readily detected by techniques known in the art.

Alternatively, a labeled component that binds to the virus may be administered to the mammal. For instance, enzyme-labeled or fluorescein-labeled anti-bodies having specific reactivity for virus epitopes may be administered to the mammal to identify and detect the presence and location of cancer cells to which the virus has bound.

The invention also provides a method of detecting cancer cells in the mammal comprising administering Paramyxovirus to the mammal, and then measuring the virus present in the body fluids or tissues of the mammal as an indication of cancer cell division or growth. The virus may be administered to the mammal as described above. After a pre-determined period of time, samples of body fluids or tissues may be removed from the mammal and tested by standard techniques known in the art, including but not limited to, plaque assays, immunoassays of viral antigens, and polymerase chain reaction to detect portions of the viral genome. Using such techniques, the presence, if any, of the virus, viral antigens or viral nucleic acid can be detected and/or quantitated. In a preferred method, NDV levels are detected and quantified about one day to about four days after administration. Applicants believe that the quantitation of virus in the mammal, after administration of the virus, will correlate with tumor burden in the mammal and may be used to screen for occult tumors or cancers within the mammal, as well as to quantitate the amount of cancer within the mammal.

The invention also provides a genetically engineered Paramyxovirus. The engineered virus is preferably a lytic Paramyxovirus so that the virus can select the cancer cells and initiate a lytic infection within the cancer cells. More preferably, the engineered virus is NDV. The engineered viruses of the invention can replicate and amplify the number of viruses, thereby increasing the efficiency of gene product translation and expression.

The engineered viruses are useful for delivering heterologous nucleic acid to host cancer cells or cancer cell sites. The heterologous nucleic acid delivered by the engineered Paramyxovirus to the host cells is not inserted into the genome of the host cells. Transcription of RNA from the heterologous nucleic acid occurs in the host cell cytoplasm, independent of the cell cycle kinetics, and can therefore produce relatively large amounts of heterologous gene product locally at the situs of host cancer cells. This is especially advantageous, for instance, for delivering heterologous nucleic acid encoding biologically or chemically active proteins like IL-2 and TNF which possess anti-tumor properties but tend to have high toxicity levels systemically. It is also advantageous for delivering heterologous nucleic acid encoding drug susceptibility genes like the herpes virus thymidine kinase gene. Ram et al., (1993) *Cancer Research*, 53, 83-88; Culver et al., (1992), *Science*, 256, 1550-1552. Using the engineered viruses of the invention, the heterologous nucleic acid can be delivered to and expressed in appropriate levels within cancer cell tumors or at cancer cell sites.

The genetically engineered virus of the invention comprises heterologous nucleic acid. "Heterologous nucleic acid" is defined herein to mean nucleic acid from a source other than the virus itself and the host cell which is to receive the heterologous nucleic acid. The heterologous nucleic acid or its complementary sequence will preferably comprise an open reading frame ("ORF"). The term "open reading frame" as used herein refers to a region of nucleotide sequence which encodes a polypeptide; this region may represent a portion of a coding sequence or a total coding sequence. A "coding sequence" as referred to herein is a nucleotide sequence which is transcribed into mRNA and/or translated into a peptide, polypeptide, or protein when placed under the control of an appropriate regulatory or control sequence. The boundaries of the coding sequence are determined by a translation start codon at the 5' terminus and a translation stop codon at the 3' terminus. A coding sequence can include but is not limited to mRNA, cDNA and recombinant polypeptide sequences.

In a preferred embodiment, the heterologous nucleic acid or its complementary sequence includes an open reading frame encoding one or more of the agents described above, including but not limited to IL-2, TNF, IL-4, gamma interferon, GM-CSF, and drug susceptibility genes such as the herpes thymidine kinase gene. The open reading frame may also encode for other biologically or chemically active proteins. The nucleic acid sequences encoding many of the agents described above are known in the art [See, for example, Taniguchi et al., (1983) *Nature*, 302, 305-310] and can be produced using techniques in the art, such as molecular cloning and phosphoramidite chemistry.

The heterologous nucleic acid is operatively linked to one or more control sequences compatible with the virus and host cell. The term "control sequence" used in the present application refers to a nucleotide sequence which is necessary to effect expression of coding sequence(s) to which it is ligated. Examples of such control sequences include promoter, terminator, enhancer and leader sequences. "Operatively linked" refers to a relationship among or between sequences permitting them to function in their intended manner. For instance, a control sequence operatively linked to a coding sequence is ligated in such a way that expression of the coding sequence is achieved under conditions compatible with the control sequence. The control sequences can be at either or both ends of the heterologous nucleic acid, open reading frame, or coding sequence. A preferred promoter in a genetically engineered NDV is the NDV's conserved start signal at the beginning of the heterologous gene and terminated with a conserved polyadenylation signal. See, Miller et al., *Newcastle Disease*, 1988 Kluwer Academic Publishers, pp. 79-97. The control sequence(s) may be purified or isolated, or may be synthesized.

The heterologous nucleic acid and control sequence(s) may be inserted within the Paramyxovirus genome, or parts thereof, using techniques that are well known in the art. The heterologous nucleic acid is preferably inserted in the Paramyxovirus genome as a substitution for, or next to, the NP gene since the NP gene is maximally expressed during viral infection. See, Miller et al., *Newcastle Disease*, 1988 Kluwer Academic Publishers, pp. 79-97. It is contemplated that there may be deletions and/or insertions in the viral sequence facilitating the expression of the heterologous nucleic acid. See, Park et al., (1991) *Proc. Natl. Acad. Sci.*, 88, 5537. Those skilled in the art can determine without undue experimentation the minimum number or length of sequences or sites of insertion which are required to allow functional integration of the heterologous nucleic acid into the viral genome. Insertion of the heterologous nucleic can then be determined by techniques known in the art such as Southern blot analysis.

The expression of the heterologous nucleic acid can be monitored by various methods known in the art. The selected method will depend, of course, on the nature of the heterologous nucleic acid and its gene product. That selection can be made empirically by those skilled in the art. Examples of these methods include immunological and chemical assays.

The invention further provides an article of manufacture and kit containing materials useful for treating and detecting cancer. The article of manufacture comprises a container with a label. Suitable containers include, for example, bottles, vials, and test tubes. The containers may be formed from a variety of materials such as glass or plastic. The container holds a composition which is effective for treating and detecting cancer. The active agent in the composition comprises NDV, and preferably comprises purified NDV or genetically engineered NDV. The label on the container indicates that the composition is used for treating and detecting cancer, and may also indicate directions for either in vivo or in vitro use, such as those described above.

The kit of the invention comprises the container described above and may further include other materials desirable from a commercial and user standpoint, including but not limited to buffers, diluents, filters, needles, syringes, cell culture medium and culture vessels.

EXAMPLES

Example #1

Treatment of Human Tumors in Athymic Mice with Intralesional NDV

Female athymic Balb-c mice were obtained from Life Sciences, Incorporated, St. Petersburg, Fla. and Charles River Laboratories, Wilmington, Mass. They were housed in an isolated room in sterilized, filtered cages and given autoclaved-sterilized chow and water ad libitum. The care of these animals and the experimental protocols were conducted according to guidelines established by the Institutional Animal Care Committees, Cook County Hospital and Rush-Presbyterian-St. Luke's Medical Center, Chicago, Ill. Mice were obtained at approximately four weeks of age, and allowed to acclimate to their new environment for one week.

Tumor cell lines were obtained frozen from the American Type Culture Collection, Rockville, Md., and were derived from human tumors. The cell lines were maintained in Opti-MEM (Gibco-BRL, Grand Island, N.Y.) containing 2.4 g/L sodium bicarbonate, 10% heat-inactivated fetal calf serum and 1/100 dilutions of the following 100× solutions: MEM non-essential amino acids (Gibco BRL catalogue number 320-1140AG); L-glutamine (Gibco BRL catalogue number 320-5030AG); and antibiotic-antifungal (Gibco BRL catalogue number 600-5240AG). The cells were placed into 225 $mm^2$ culture flasks and incubated at 37° C. in 5% $CO_2$ to allow for adequate cell growth. The cells were then harvested by brief treatment with 0.25% trypsin (Gibco BRL, Grand Island, N.Y.), washed in serum-free medium, and counted. The cells were then placed into serum-free medium at a concentration of $1\times10^7$ cells/0.1 milliliter in preparation for injection into the animals.

Under clean conditions, the tumor cells were then implanted into the subcutaneous space on the flank of the experimental animals by injecting 0.1 ml of solution containing $1\times10^7$ cells with a 25 gauge needle. The animals were then placed back in their cages, and the tumor cells were allowed to grow in the animals.

After approximately 10 days, tumors of 6.5 mm in diameter or greater were obtained in over 90% of animals. Animals bearing tumors of at least 6.5 mm in greatest diameter were randomly divided into three groups, marked, and the tumor dimensions carefully recorded by an independent observer.

NDV strain 73-T was obtained from William A. Cassel, Atlanta, Ga. and prepared as follows. Approximately 1000 plaque-forming units (PFU) of live virus particles were injected into 10-day old chick embryos (SPAFAS, Inc., Roanoke, Ill.). The eggs were incubated for 48 hours, during which time the virus replicated rapidly, killing the majority of the eggs. The allantoic fluid was then harvested from the embryos. Contaminating red cells, embryonic membranes and egg shell debris were removed from the allantoic fluid by two low speed centrifugations at 7,520×g for 15 minutes each. The supernatant containing virus was then ultracentrifuged at 50,000×g for 18 hours. The resulting virus pellet was then resuspended in Hank's Balanced Salt Solution (HBSS) (Gibco BRL, Grand Island, N.Y.). A discontinuous sucrose gradient was prepared at concentrations of 20% and 55%, and the virus suspension was placed on the gradient and centrifuged for 1 hour at 75,000×g. The purified NDV stock was harvested from the 20%-55% interface and stored at −80° C.

Virus dose is usually expressed in plaque-forming units (PFU), or the number of infectious virus particles that are capable of replicating within and lysing cells. PFU's were measured in a plaque assay. Monolayers of HT 1080 human fibrosarcoma cells (American Type Culture Collection, Rockville, Md.) or chick embryo cells (SPAFAS, Inc., Roanoke, Ill.) were formed on 50 mm plastic tissue culture plates in Opti-MEM cell culture medium enriched with non-essential amino acids, glutamine, antibiotic-antimycotic, and 10% heat-inactivated fetal calf serum. Serial dilutions of virus in Hank's Balanced Salt Solution (HBSS) were added to the monolayers, and the virus particles were allowed to adsorb for 45 minutes at room temperature. If chick embryo cells were used, the monolayers were then sealed with a mixture of 0.9% Bacto-Agar (Difco, Detroit, Mich.) in culture medium. If HT 1080 cells were used, only cell medium was required. The monolayers were then incubated at 37° C. in 5% $CO_2$ for 18 hours (for HT 1080 cells) or 2 days (for chicken embryo cells). All agar was removed and the cells were fixed with 100% methanol and stained with 0.2% crystal violet.

Clear areas on the monolayer, called plaques, represent the lytic effect of one infectious virus particle following replication within the cell monolayer. The number of plaques were counted, and the PFU/ml was calculated based upon the dilution factor for that plate.

The purified NDV stock was diluted in a saline solution (e.g., phosphate buffer saline, PBS) at a concentration of $1\times10^7$ PFU/0.1 ml. The solution was divided into two groups, and one was treated by exposure to ultraviolet light to inactivate the viral genome. A third aliquot of saline alone was also prepared. The UV-killed virus and plain saline served as controls.

The three groups of animals were each treated by one of the three solutions described above, as follows. The tumor-bearing animal was thoroughly cleaned with alcohol, and the treatment solution was injected uniformly into the tumor using a 25 gauge needle and tuberculin syringe. The animals were then placed back into their respective cages again and observed. Every three days, the animals were examined by a blinded independent observer, who recorded tumor size of each animal in each group and calculated tumor volume $\{(\pi\times L\times H\times W)/6)\}$.

The results of these experiments are summarized in FIGS. 1-3. The animals treated with live NDV experienced complete tumor regression within 30 days of treatment, while the animals treated with UV-inactivated virus or saline alone had unabated growth of their tumors.

In the case of neuroblastoma (IMR-32) (FIG. 1) complete tumor regression was observed in 18 out of 20 mice treated once with live NDV. Tumors in the other two mice regressed, but not completely, and required a second treatment 10 days later for complete regression. At day 23, one tumor that had completely disappeared began to regrow but a second virus treatment at day 23 led to a long-lasting complete regression. No tumor regression was observed in any of 8 mice treated with UV-killed NDV or in any of 19 mice treated with saline [P<0.001 (by Fisher's exact test) compared to the group treated with live NDV].

FIG. 2 shows the intralesional therapy of established HT 1080 human fibrosarcoma xenografts (≦0.6 cm) in athymic mice using NDV (N=10, $10^7$ PFU) or saline control (PBS, N=9). After a single treatment with live NDV, 8 out of 10 tumors completely regressed (the average sizes of these 8 tumors are plotted separately). The other two tumors maintained their sizes between days 2 and 24 (and their average sizes are plotted separately). Unabated tumor growth was noted in all nine mice treated with placebo [P<0.005 (by Fisher's exact test) for tumor regression compared to the group receiving NDV].

FIG. 3 shows the intralesional therapy of established NCI-H460 human lung large cell carcinoma xenografts in athymic mice using live NDV (N=3, $10^7$ PFU) or saline control (N=1). Plotted separately are the tumor volumes in a logarithmic scale for each of these four mice as a function of tumor after treatment. Complete tumor regression occurred in 2 out of 3 mice treated with live NDV. The tumor in the mouse treated with saline continued to grow unabated.

In summary, these examples show that one dose of NDV, given intralesionally to athymic mice, caused complete and permanent eradication of a wide variety of human tumors, which grew unabated in the control animals. Treatment of NDV with a short exposure to UV radiation, which damaged the genetic material so that the virus cannot replicate but can still bind, was no more effective than treatment with saline alone at causing tumor regression. The live NDV-treated animals were followed out for the remainder of their natural life, and very few tumor recurrences were observed in any of the animals. The recurrent tumors, however, completely regressed after a second local treatment of NDV. In addition, no untoward effects of virus treatment was noted in any of the animals.

Example #2

Treatment of Human Tumors in Athymic Mice Using Systemic NDV Therapy

Athymic mice were injected with human tumor xenografts as described in Example #1. When tumors greater than 6 mm in diameter were achieved, the animals were divided into three groups. The NDV was prepared (see Example #1) in concentrations of $1\times10^8$ PFU/0.3 ml or $1\times10^9$ PFU/0.3 ml of saline. The control solution was an equal volume of saline alone.

The abdomens of the animals were washed thoroughly with alcohol, and the NDV was injected 1 intraperitonealy using a 25 gauge needle. One set of experimental mice (N=3) received a single injection of NDV at the higher dose ($10^9$ PFU), while the other set of 4 mice received injections of $10^8$ PFU three times per week. Control animals received injections of saline. The animals were then observed and the tumor sizes were followed as described for Example #1.

The results are summarized in FIG. 4. Six out of 7 animals treated with intraperitoneal live NDV experienced complete regression of their tumors by day 52, while the animals treated with saline alone experienced unabated tumor growth. Complete tumor regression was noted in all mice treated only once with $10^9$ PFU of NDV (- -●- -) and in 3 out of 4 mice treated multiple times with $10^8$ PFU of live NDV (- -■- -). Tumor volumes for the one mouse treated multiple times with $10^8$ PFU of NDV which did not have complete tumor regression is plotted separately (- -♦- -). All the tumors treated with PBS (- -○- -) alone showed marked tumor progression (P<0.0025, Fisher's exact test).

The results demonstrate that NDV is effective at treating cancer when administered systemically. No untoward effects were noted in the animals from treatment with live NDV.

Example #3

Treatment of Human Tumors in Athymic Mice Using Attenuated Strains of NDV

NDV strain 73-T was obtained and prepared as described in Example #1. NDV strain M (Mass-MK107) is a strain less virulent than 73-T and was obtained from Dr. Mark Peeples, Rush-Presbyterian-St. Luke's Medical Center, Chicago, Ill. Strain M was replicated in a similar manner to that described in Example #1 for NDV strain 73-T.

Athymic animals were injected with human HT1080 tumor cells subcutaneously as described above. They were allowed to develop tumors of at least 6.5 mm in diameter at which time they were randomly divided into three groups, and their tumor sizes were recorded.

The animals from one group were injected with $1.0\times10^8$ PFU of NDV strain 73-T in 0.1 ml saline intralesionally, as was described in Example #1. The second group was injected with $1.0\times10^8$ PFU of NDV strain M in 0.1 ml saline intralesionally. The last group was injected with 0.1 ml of saline alone. The animals were then observed and their tumor sizes were independently recorded every three days, as described in Example #1 above.

The results are shown in FIG. 5. As in Example #1, the tumors treated intralesionally with NDV strain 73-T disappeared completely. Two of the three tumors treated intralesionally with strain M similarly disappeared in less than three weeks. No regression occurred in control mice treated with saline.

Example #4

In vitro Assays Testing Effect of NDV on Human Cancer Cells

NDV (strain 73-T, prepared as described in Example #1) was assayed with the human cancer cell lines listed below to determine sensitivity of each of the cell types to NDV.
KB-8-5-11 Cervical Carcinoma
SW626 Ovarian Carcinoma
SK-OV-3 Ovarian Carcinoma
A172 Glioblastoma (brain cancer)
HT1080 Sarcoma (fibrosarcoma)
KHOS Sarcoma (osteosarcoma)
IMR-32 Neuroblastoma
SW620 Colon carcinoma
HT29 Colon carcinoma
NCI-460 Lung carcinoma (large cell)
NCI-H510A Lung carcinoma (small cell)
SK-MEL-3 Melanoma
SK-MEL-28 Melanoma
SCC25 Squamous cell carcinoma of head and neck
MDMBA468 Breast carcinoma
MDMBA157 Breast carcinoma
SKBR3 Breast carcinoma
PC3 Prostate carcinoma
G104 Wilm's tumor With the exception of the KB-8-5-11 Cervical Carcinoma and KHOS Sarcoma (osteosarcoma) cell lines, all the cell lines were obtained from ATCC, Rockville, Md. The KB-8-5-11 Cervical Carcinoma cell line was obtained from Dr. John Coon, Rush University, Chicago, Ill., and the KHOS Sarcoma (osteosarcoma) cell line was obtained from Dr. Warren Knudson, Rush University, Chicago, Ill. The cells and NDV were assayed according to the plaque assay described in Example #1, except that higher multiplicities of infection were used (ranging from 0.01 to 10). All of the assays were performed in parallel with control cultures treated with medium alone.

The results of the plaque assays showed that all of the cancer cell types were susceptible to cell killing by NDV. Cytolysis was observed 1 to 3 days after virus inoculation and in all cases was observed by phase contrast microscopy to consist of cell membrane disintegration and cell detachment.

Example #5

Treatment of Human Cancer Cell Tumors in Athymic Mice Using Intralesional NDV Therapy In vivo experiments were conducted in accordance with the methods and procedures described in Example #1 with the following exceptions: (1) male athymic Balb-C mice obtained from Life Sciences were used as hosts for the PC3 prostate carcinoma cells; female mice were used as hosts for all other cancer cells tested; (2) tumor tissues identified as MM17387 colon carcinoma, TH14145 synovial sarcoma, and MEL 330 melanoma were obtained from surgical pathology specimens of cancer patients at Rush-Presbyterian-St. Luke's Medical Center and passed as tumor explants in athymic mice (See, Sharkey, et al., (1978) *The Nude Mouse in Experimental and Clinical Research* (Eds.: J. Fogh & B. P. Giovanella), Academic Press., New York, Volume 1, pp. 187-214) and treated with NDV or control saline at first or second passage. KB-8-5-11 cervical carcinoma cells were obtained from Dr. John Coon, Rush University, Chicago, Ill. All other tumor cell lines described below and in FIGS. 6-14 were obtained from ATCC, Rockville, Md.

Animals treated with live NDV experienced tumor regression or stabilization within 30 days of treatment, while the animals treated with UV-inactivated virus or saline alone had unabated growth of their tumors. The in vivo results showed that a single dose of NDV given intralesionally to athymic mice caused regression or growth inhibition of a wide variety of cancer cell tumors and that those cancer cell tumors grew unabated in control animals. No adverse side effects of virus treatment were noted in any of the animals. The results of the in vivo experiments are summarized in FIGS. 6-14.

In the case of glioblastoma (U87MG) (FIG. 6), complete tumor regression was observed in 4 out of 4 mice treated once with live NDV. No tumor regression was observed in the one mouse treated with PBS.

FIG. 7 shows the intralesional therapy of established KB8-5-11 cervical carcinoma xenografts using live NDV (N=12, $10^7$ PFU), UV-killed NDV (N=12), or saline control (PBS, N=12). After a single injection of live NDV, a marked growth inhibition was observed in all 12 mice. Unabated tumor growth was seen in all 12 mice treated with saline. A slight growth inhibition was seen in the mice treated with UV-killed virus.

FIG. 8 shows the regression of four NPC-3 human prostate carcinoma xenografts following intratumor injection with live NDV. The tumors in the mice treated with PBS continued to grow unabated.

FIGS. 9, 10 and 11 show the growth inhibition of HT29 colon carcinoma, SK-BR-3 breast carcinoma, and SW620 colon carcinoma xenografts following injection with live NDV compared to saline control.

FIG. 12 shows the growth inhibition of three MM17387 colon carcinoma xenografts (at second passage from the patient) following injection with live NDV compared to saline control. Three mice treated intratumorally with UV-killed NDV showed a lesser degree of growth inhibition.

FIG. 13 shows the intralesional therapy of established low-passage (passage #1 or 2) human TH14145 synovial sarcoma xenografts in athymic mice. Greater than 90% tumor regression was observed in six out of 9 mice treated with live NDV. No tumor regression was observed in any of the four mice treated with saline.

FIG. 14 shows the regression of a single MEL330 human melanoma xenograft in an athymic mouse following intratumor injection with NDV. Tumor progression was seen in the one mouse treated with saline.

What is claimed is:

1. A method of treating cancer in a mammal having a tumor comprising administering intravenously to said mammal more than one dose of a composition comprising live Newcastle Disease Virus in an amount sufficient to cause tumor regression, wherein said composition is essentially free of allantoic fluid.

2. A method of treating cancer in a mammal having a tumor comprising administering to said mammal more than one dose of a pharmaceutical composition comprising live purified Newcastle Disease Virus in an amount sufficient to cause tumor regression, wherein said live purified Newcastle Disease Virus is administered systemically not directly at the tumor site.

3. The method of claim 1 or 2, wherein said tumor is selected from the group consisting of lung carcinoma, breast carcinoma, prostate carcinoma, endometrial carcinoma, ovarian carcinoma, bladder carcinoma, Wilm's tumor, fibrosarcoma, osteosarcoma, synovial sarcoma and glioblastoma.

4. The method of claim 1 or 2, wherein said tumor is colon adenocarcinoma.

5. The method of claim 1 or 2, wherein said tumor is melanoma.

6. The method of claim 1 or 2, wherein said tumor is neuroblastoma.

7. The method of claim 1 or 2, wherein said Newcastle Disease Virus is strain Mass MK107.

8. The method of claim 1 or 2, wherein said Newcastle Disease Virus is strain 73-T.

9. The method of claim 1 or 2, wherein the amount of Newcastle Disease Virus administered is about $4 \times 10^{10}$ to $4 \times 10^{12}$ PFU/kg.

10. The method of claim 1 or 2, wherein the Newcastle Disease Virus is administered in an amount of $10^8$ PFU.

11. The method of claim 1 or 2, further comprising administering a chemotherapeutic agent.

12. The method of claim 11, wherein the chemotherapeutic agent is selected from the group consisting of thiotepa, busulfan, cyclophosphamide, methotrexate, cytarabine, bleomycin, cisplatin, doxorubicin, melphalan, mercaptopurine, vinblastine, paclitaxel and retinoic acid.

13. The method of claim 11, wherein the chemotherapeutic agent is 5-fluorouracil.

14. The method of claim 1 or 2, further comprising administering an immunosuppressive agent.

15. The method of claim 14, wherein said immunosuppressive agent is a corticosteroid.

16. The method of claim 1 or 2, further comprising administering a cytotoxic or cytostatic agent.

17. The method of claim 16, wherein said cytotoxic or cytostatic agent is an antibody.

18. The method of claim 16, wherein said cytotoxic or cytostatic agent is a cytokine.

19. The method of claim 1 or 2, wherein said Newcastle Disease Virus is purified from cell culture.

20. The method of claim 1 or 2, wherein said tumor is cervical carcinoma.

21. The method of claim 1 or 2, wherein said composition also comprises a pharmaceutically acceptable carrier.

22. The method of claim 1 or 2, wherein said tumor is a human tumor.

23. The method of claim 1 or 2, wherein said tumor is greater than 0.6 cm in diameter.

24. The method of claim 1 or 2, wherein said tumor is a metastatic tumor.

25. The method of claim 1 or 2, further comprising administering radiation.

* * * * *